US009597391B2

(12) United States Patent
Ebensen et al.

(10) Patent No.: US 9,597,391 B2
(45) Date of Patent: Mar. 21, 2017

(54) CYCLIC-DINUCLEOTIDES AND ITS CONJUGATES AS ADJUVANTS AND THEIR USES IN PHARMACEUTICAL COMPOSITIONS

(75) Inventors: Thomas Ebensen, Hannover (DE); Michael Morr, Wolfenbuettel (DE); Carlos A. Guzman, Wolfenbuettel (DE)

(73) Assignee: HELMHOLTZ_ZENTRUM FUER INFEKTIONSFORSCHUNG GMBH, Braunschweig (DE)

( * ) Notice: Subject to any disclaimer, the term of this patent is extended or adjusted under 35 U.S.C. 154(b) by 1210 days.

(21) Appl. No.: 12/092,747

(22) PCT Filed: Nov. 8, 2006

(86) PCT No.: PCT/EP2006/010693
§ 371 (c)(1),
(2), (4) Date: May 6, 2008

(87) PCT Pub. No.: WO2007/054279
PCT Pub. Date: May 18, 2007

(65) Prior Publication Data
US 2008/0286296 A1    Nov. 20, 2008

(30) Foreign Application Priority Data
Nov. 8, 2005 (EP) .................................. 05024266

(51) Int. Cl.
| | | |
|---|---|---|
| A61K 39/39 | (2006.01) | |
| A61K 39/00 | (2006.01) | |
| A61P 37/00 | (2006.01) | |
| A61K 31/7084 | (2006.01) | |
| A61K 31/7076 | (2006.01) | |

(52) U.S. Cl.
CPC .......... *A61K 39/39* (2013.01); *A61K 31/7076* (2013.01); *A61K 31/7084* (2013.01); *A61K 2039/55511* (2013.01)

(58) Field of Classification Search
CPC ................ A61K 31/7084; A61K 39/39; A61K 31/7076; A61K 2039/55511
USPC ......... 514/48, 45, 42; 536/22.1, 26.74, 18.7, 536/26.13; 424/194.1, 193.1, 184.1
See application file for complete search history.

(56) References Cited

U.S. PATENT DOCUMENTS

2004/0097719 A1* 5/2004 Agrawal et al. ............. 536/23.2

FOREIGN PATENT DOCUMENTS

| WO | WO03/084568 | 4/2003 |
|---|---|---|
| WO | WO 2004/009125 | 1/2004 |
| WO | WO 2004/108634 A2 * | 12/2004 |
| WO | WO 2005/087238 A | 9/2005 |

OTHER PUBLICATIONS

Krahmer et al.; WO 2004/108634 A2; Dec. 16, 2004 (English Machine Translation).*
Gura (Science, Nov. 1997, 278(5340):1041-1042).*
Jain (Sci. Am., 1994, 271:58-65).*
Curti (Crit. Rev. in Oncology/Hematology, 1993, 14:29-39).*
Hsu et al. (Nucleosides & Nucleotides (1985), 4(3), 377-89) (abstract sent).*
McGhee et al. "The muscosal immune system: from fundamental concepts to vaccine development", Vaccine, vol. 10, Issue 2, 1992, pp. 75-86 Vajdy et al. "Muscosal Adjuvants and Delivery Systems for Protein-, DNA- and RNA-based Vaccines", Immunology and Cell Biology (2004) 82, jpp. 617-627.
Banchereau, J., et al., "Dendritic cells and the control of immunity", Nature, vol. 392, Mar. 1998 (pp. 245-252).
Ebensen, T., et al., "The bacterial second messenger cdiGMP exhibits promising activity as a mucosal adjuvant", Cl. & Vaccine Imm, vol. 14, No. 8, Aug. 2007 (pp. 952-958).
Ebensen, T., et al., "Bis-(3',5')-cyclic dimeric adenosine monophosphate: Strong Th1/Th2/Th17 promoting mucosal adjuvant", Vaccine, vol. 29, 2011 (pp. 5210-5220).
Egli, A., et al., "Vaccine adjuvants—understanding molecular mechanisms to improve vaccines", Swiss Medical Weekly, 2014:213940 (pp. 1-16).
Elenkov, I.J., "Glucocorticoids and the Th1/Th2 Balance", NY Acad. Sci. 1024: 2004 (pp. 138-146).
Gray, P.M., et al., "Evidence for cyclic diguanylate as a vaccine adjuvant with novel immunostimulatory activities", Cellular Immunology vol. 278, 2012 (pp. 113-119).
Libanova, R., et al., "The member of the cyclic di-nucleotide family bis-(3', 5')-cyclic dimeric inosine monophosphate exerts potent activity as mucosal adjuvant", Vaccine, vol. 28, 2010, (pp. 2249-2258).
McKinstry, K.K., et al., "Memory CD4 T cell-mediated immunity against influenza A virus: more than a little helpful", NIH Public Access, Arch Immunol Ther Exp (Warsz), Oct. 2013, 61(5) (pp. 1-22).
Neurath, M.F., et al., "The role of Th1/Th2 polarization in mucosal immunity", Nature Medicine, vol. 8, No. 6, Jun. 2002, (pp. 567-573).

(Continued)

*Primary Examiner* — Shaojia Anna Jiang
*Assistant Examiner* — Michael C Henry
(74) *Attorney, Agent, or Firm* — Whitham, Curtis & Cook, P.C.

(57) ABSTRACT

The present invention relates to new adjuvants and the uses in pharmaceutical compositions, like in vaccines. In particular, the present invention provides new compounds useful as adjuvants and/or immunomodulators for prophylactic and/or therapeutic vaccination in the treatment of infectious diseases, inflammatory diseases, autoimmune diseases, tumors, allergies as well as for the control of fertility in human or animal populations. The compounds are particularly useful not only as systemic, but preferably as mucosal adjuvants. In addition, the invention relates to its uses as active ingredients in pharmaceutical compositions.

12 Claims, 14 Drawing Sheets

(56) References Cited

OTHER PUBLICATIONS

Pinto, R.A., et al., "T Helper 1/T Helper 2 Cytokine Imbalance in Respiratory Syncytial Virus Infection is Associated with Increased Endogenous Plasma Cortisol", Pediatrics, Apr. 17, 2006, (pp. e878-e-887).

Riese, P., et al., "Vaccine Adjuvants: Key Tools for Innovative Vaccine Design", Current Topics in Medical Chemistry, vol. 13, 2013, (pp. 2562-2580).

Yin, Q., et al., "Cyclic di-GMP Sensing via the Innate Immune Signaling Protein STING", Molecular Cell, vol. 46, Jun. 29, 2012, (pp. 735-745).

Ebensen et al. The Bacterial Second Messenger Cyclic diGMP Exhibits Potent Adjuvant Properties, Vaccine 25, 2007, pp. 1464-1469.

* cited by examiner

Fig.: 1

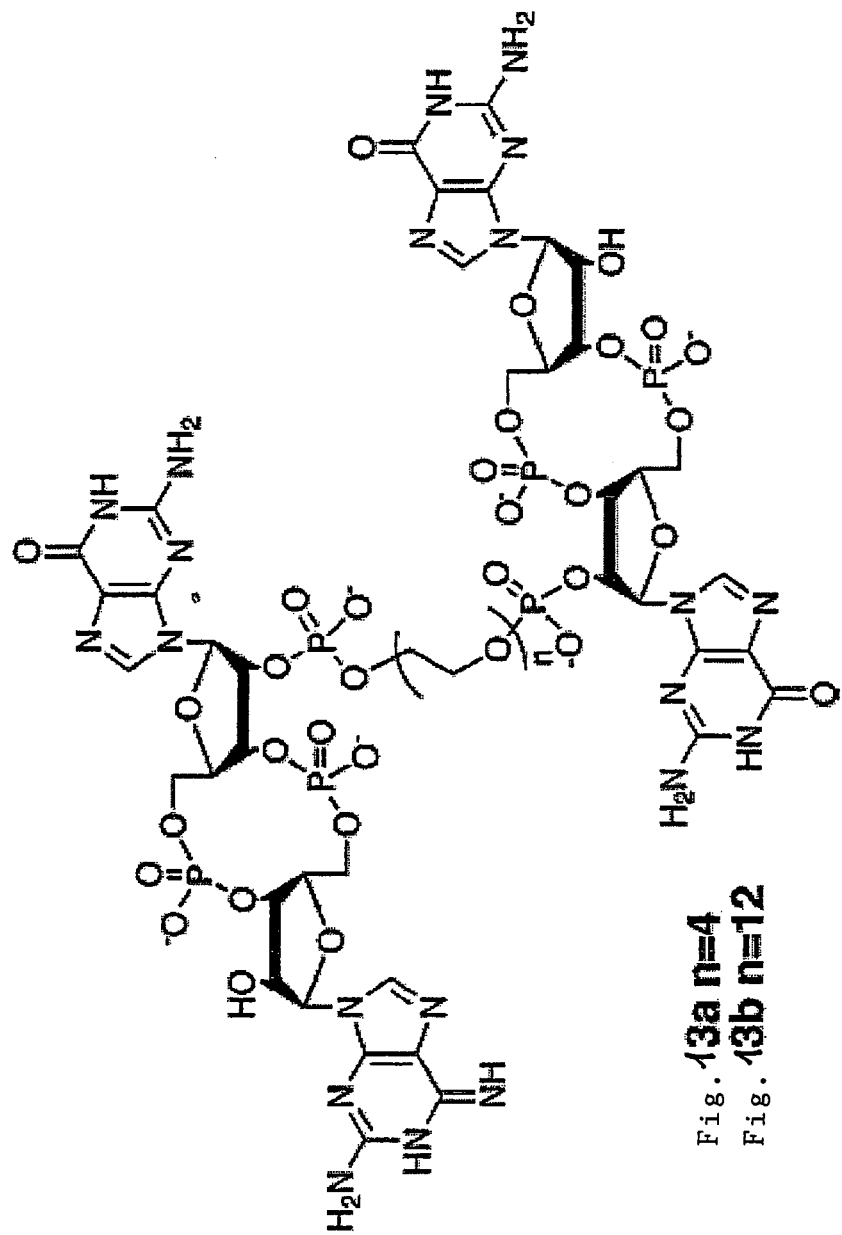
Fig. 13a n=4
Fig. 13b n=12

CYCLIC-DINUCLEOTIDES AND ITS CONJUGATES AS ADJUVANTS AND THEIR USES IN PHARMACEUTICAL COMPOSITIONS

FIELD OF THE PRESENT INVENTION

The present invention relates to new adjuvants and their uses in pharmaceutical compositions, like in vaccines. In particular, the present invention provides new compounds useful as adjuvants and/or immunomodulators for prophylactic and/or therapeutic vaccination in the treatment of infectious diseases, inflammatory diseases, autoimmune diseases, tumors, allergies as well as for the control of fertility in human or animal populations. The compounds are particularly useful not only as systemic, but preferably as mucosal adjuvants. In addition, the invention relates to its uses as active ingredients in pharmaceutical compositions.

BACKGROUND OF THE INVENTION

Infectious diseases are the major cause of morbidity and mortality, accounting for a third of the deaths which occur in the world each year. In addition, infectious agents are directly responsible for at least 15% of new cancers, and they also seem to be involved in the pathophysiology of several chronic diseases (e.g. inflammatory, vascular and degenerative diseases). Traditional infectious diseases are also highly expensive in terms of health-associated costs of infected patients and loss in productivity at work.

The main strategies used to prevent infectious diseases are therapy and prophylaxis. Vaccination has become the most cost-effective measure to prevent infections. However, there are still many diseases for which vaccines are not yet available or the available vaccines are not completely satisfactory due to low efficacy, high reactogenicity, poor stability and/or high costs. Thus, there is still an urgent need for both new and improved vaccines.

Despite the fact that vaccines have traditionally been used for the prophylaxis of infectious diseases, recent findings suggest that they are also a powerful tool for the immuno-therapy of transmissible diseases (e.g. viral hepatitis, *Helicobacter pylori* infections, herpes virus infections, etc.). In addition, vaccines can be used for the immune-therapy or immune-prophylaxis of autoimmune diseases, inflammatory diseases, tumors, allergies and for the control of fertility in human and/or animal populations. In particular, the latter application seems to require the elicitation of efficient mucosal responses at the level of the reproductive tract.

Most infectious diseases are either restricted to the mucosal membranes or the etiologic agents need to transit the mucosa during the early steps of the infection. Therefore, it is desirable to obtain not only a systemic, but also a local mucosal immune response as a result of vaccination, thereby blocking both infection (i.e. colonization) and disease development. This may result in a more efficient protection against infection, facilitating also the eradication of diseases for which humans are the only reservoirs (i.e. blocking transmission to susceptible hosts). Parenterally-administered vaccines mainly stimulate systemic responses, whereas vaccines administered by a mucosal route mimic the immune response elicited by natural infections and can lead to efficient mucosal and systemic responses. Due to the apparent compartmentalization of the systemic and mucosal immune system, parenterally administered vaccines are less effective in protecting against mucosal pathogens (McGhee, J. R., Mestecky, J., Dertzbaugh, M. T., Eldridge, J. H., Hirasawa, M. and Kiyono, H. (1992) The mucosal immune system: from fundamental concepts to vaccine development. Vaccine 10, 75-88). Thus, administration of immunogens through the mucosal route is required to achieve full protection. However, most of the available vaccines are administered through the parenteral route, thereby, eliciting a systemic immunity in the individual.

The administration of vaccines via the mucosal route offers several advantages over parenteral vaccination. These advantages include an ease of administration, the possibility of self-administration (e.g. by intranasal, rectal or oral application), the elimination of the chance of unwanted cross-infection due to the use of infected needles or non-sterile working, lower rates of side effects, higher acceptance by the public, better compliance of vaccination protocols (i.e. increment in the overall efficacy), simpler administration logistics and lower delivery costs, being particularly suitable for mass immunization programs. However, the compartmentalization at the level of the mucosal immune system has to be taken into consideration. In fact, immune responses which can be observed following intranasal vaccination may not necessarily occur after oral or intra-rectal immunization. For example, oral vaccination may not stimulate efficient responses in the genitourinary and/or respiratory tracts.

Unfortunately, the delivery of antigens by the mucosal route is associated with a major problem, namely that antigens delivered by this route are generally poorly immunogenic. This is the result of different mechanisms, such as (i) accelerated antigen elimination by the non specific host clearance mechanisms (e.g. ciliar activity, peristaltism), (ii) antigen degradation by local enzymes, (iii) antigen alteration and/or structural modification as a result of extreme pH (e.g. acidic in the stomach, alkaline in the intestine), (iv) poor antigen penetration through the mucosa, (v) limited access of vaccine antigens to antigen presenting cells, and (vi) local peripheral tolerance.

To overcome these problems, different strategies have been used, such as antigen entrapment or association with physical or biological particles (e.g. microparticles, nanoparticles, bacterial ghosts), the use of virosomes or viral-like-particles, the use of liposomes or ISCOMS, the use of transgenic plants, antigen production by attenuated viral or bacterial carriers acting either as conventional vectors or as carriers for nucleic acid vaccines and/or their administration with mucosal adjuvants. However, despite the heavy body of experimental evidence generated in pre-clinical studies during the last years, almost no candidates have been transferred to the vaccine development pipeline.

The use of optimal adjuvants plays a crucial role in vaccination. Antigens administered without adjuvant only rarely mediate an adequate immune response. In addition, not only the strength but also the quality of the elicited immune response matters. Stimulation of an incorrect immunization pattern may lead to immunopathological reactions and exacerbation of the symptoms of infection. In this context, the adjuvant can help to assist the desired immune response. In other words, an adjuvant can modulate the immune response or redirect the immune response to balance the immune response in the desired direction.

Substances referred to as "adjuvants" are those which are added and/or co-formulated in an immunization to the actual antigen (i.e. the substance which provokes the desired immune response) in order to enhance the humoral and/or cell-mediated immune response ("Lexikon der Biochemie und Molekularbiologie", 1. Band, Spektrum, Akademischer Verlag1995). That is, adjuvants are compounds having immunopotentiating properties, in particular, when co-administered with antigens. The use of many adjuvants is based solely on experience, and the effect can neither be accurately explained nor predicted. The following groups of adjuvants are traditionally used in particular: aluminum hydroxide, emulsions of mineral oils, saponins, detergents, silicon compounds, thiourea, endotoxins of gram-negative bacteria, exotoxins of gram-positive bacteria, killed or attenuated living bacteria or parts thereof.

An overview over the presently known mucosal adjuvants and delivery systems, e.g. the above mentioned particles, ICOMS, liposomes and viral-like particles, for protein-, DNA- and RNA-based vaccines is given in Vajdy et al., Immunol. Cell Biol., 2004, 82, 617- 627. Therein the currently available approaches in immunopentiation of mucosal vaccines are discussed.

That is, various mucosal adjuvants have been described which should serve as an alternative for the adjuvants useful for systemic administration, e.g. see Vajdy et al., supra. These mucosal adjuvants include heat labile enterotoxin and detoxified mutants thereof. In particular, genetically detoxified mutants of heat labile enterotoxin of *E. coli* have been developed as useful mucosal adjuvants. Moreover, cholera toxin of vibrio cholera is known as an adjuvant useful for mucosal vaccination. Further, the application of unmethylated CpG dinucleotides has been described. It was shown that CpG can bias the immune response towards a Th1 response and can modulate pre-existing immune responses. Saponins are also described as immunomodulatory substances, predominantly via the induction of specific cytokines which then modulate and/or activate the immune response.

In addition, as adjuvants which may be useful in mucosal vaccination the following have been described:

The MALP-2 molecule and Bisaxcyloxypropylcysteine-conjugates thereof, e.g. a Bispalmitoyloxypropylcysteine-PEG molecule is known to represent potent stimulants for macrophages. The usefulness of MALP-2 as an adjuvant was shown previously, see e.g. WO2004/009125 and WO2003/084568. In particular, it was demonstrated that MALP-2 can act as an effective mucosal adjuvant enhancing the mucosal immune response, e.g. fostering an enhanced expression of antigen-specific IgA antibodies.

Furthermore, it was shown that MALP-2 can activate dendritic cells and B-cells, both play an important role in the induction of a specific humoral immune response. In addition, preliminary studies demonstrate that a combination of biologically active HIV-1 tat protein and synthetic MALP-2 may be a promising vaccine with the MALP-2 component as an effective mucosal adjuvant.

Unfortunately, most of the compounds described above being useful as mucosal adjuvants are not utilizable due to their intrinsic toxicity, e.g. retrograde homing to neuronal tissues of bacterial toxoids and/or toxins at/in the derivatives after nasal vaccination.

Thus, none of these previously described mucosal adjuvants have been approved yet, but, today, only two systemic adjuvants received approval to be administered to humans and, hence, are used for the preparation of human vaccines. These adjuvants are Alum and MF59. However, both are not effective as mucosal adjuvants.

There has been an intensive search in recent years for novel adjuvants, including those for the mucosal administration route. Only a few substances have been found to be able to enhance mucosal responses. Among these, some act as carriers to which the antigens must be bound or fused thereto. Far fewer universally employable "true" adjuvants which are admixed to the antigens have been found, as outlined above.

Prokaryotic as well as eukaryotic cells use various small molecules for cell signaling and intra- and intercellular communication. For example, cyclic nucleotides like cGMP, cAMP, etc are known to have regulatory and initiating activity in pro- and eukaryotic cells. While in eukaryotic cells cAMP and cGMP are used as signaling molecules, prokaryotic cells utilize cyclic di-nucleoside mono phosphate molecules, in particular cyclic diguanosine-monophosphate (c-diGMP) beside cAMP.

The condensation of two GTP molecules is catalyst by the enzyme diguanylate cyclase (DGC) to give c-diGMP. C-diGMP has been described as a molecule having antimicrobial activity und may be used to prevent or combat pathogens. Moreover, it was shown that c-diGMP represents one of the key regulators in bacteria. Further, it is known that eukaryotic cells do not use the c-diGMP molecule in its biochemical pathways. In bacterial cells, c-diGMP regulates the expression of genes and the biosynthesis of exo-polysaccharides. Since interacting ligands of c-diGMP are expressed throughout the various genuses of bacteria, it is assumed that most bacteria use c-diGMP as a regulatory molecule.

In WO 2005/087238, it has been speculated that cyclic diGMP or analogs thereof can stimulate or enhance immune or inflammatory response in a patient or can enhance the immune response to a vaccine by serving as an adjuvant. Further, it is speculated that cyclic diGMP or its analogs may be used as active ingredient in compositions for treating injuries, diseases, disorders and conditions that result in neurodegeneration. Therein, data are provided showing that cyclic diGMP does not modulate DC endocytic activity but may activate dendritic cells due to induction of expression of co-stimulatory molecules. Further, data are provided showing that occasionally c-diGMP may upregulate immunostimulatory capacity of dendritic cells. Further, data are provided showing that c-diGMP in high doses may activate T-cells in vitro when mixed with dendritic cells. However, any enhancement of immune or inflammatory responses in a patient or enhancement of the immune response to a vaccine by serving as an adjuvant is not shown, rather it is speculated therein that there are some data which may indicate for an increased presentation of antigen through stimulation of HLA-DR. Further, no immunomodulatory action of cyclic diGMP is shown in said document. Hence, this document merely speculates about any immunomodulatory, in particular, about any enhanced immune response by serving as an adjuvant. As discussed before, an adjuvant is a compound able to provoke or enhance the humoral and/or cell mediated immune response against an active antigen. No data are provided in WO 2005/087238 showing an immune response against an active antigen using c-diGMP as adjuvant for enhancing or eliciting or modulating said immune response. In addition, it is noted that said document only provides information regarding c-diGMP but not with respect to any other analogs of cyclic diGMP.

Hence, there is still a need in the prior art to provide new compounds useful as adjuvants, particularly as mucosal adjuvants and/or as vaccines. In particular, there is a need for mucosal adjuvants which can elicit a strong immune response which represent a balanced or adjusted immune response involving both humoral and cellular components, thus, allowing effective prophylaxis or treatment of various diseases and conditions, specifically of infectious diseases or cancer.

Thus, the object of the present invention is the provision of mucosal adjuvants which can elicit and/or enhance and/or modulate (pre-existing) immune response in an individual or subject. In particular, the invention was based on the object of developing a range of novel, highly active adjuvants, particularly mucosal adjuvants which are non-toxic for humans and which can be employed with a wide variety of active ingredients to be assisted in conventional or novel vaccines such as, in particular, prophylactic or therapeutic vaccines, including cancer and DNA vaccines.

DESCRIPTION OF THE INVENTION

This technical problem is solved by the provision of the embodiments as characterized in the claims.

The present invention is generally concerned with the provision of new compounds and conjugates as depicted in formula (I) or salts or solvates thereof, useful as immunomodulatory compounds, in particular, as adjuvants, preferably as mucosal adjuvants. Furthermore, the present invention relates to new pharmaceuticals comprising at least one of the conjugates according to formula (I) as described herein, with pharmaceutically acceptable carrier(s), optionally together with additional active ingredients.

That is, the present invention relates to the provision of the use of specific compounds or conjugates useful as adjuvants in therapeutic or prophylactic vaccination. Said compounds and conjugates are useful as systemic and are particularly useful as mucosal adjuvants being applied via the mucosa of the individual.

The present inventors now found that bacterial signaling molecules are useful as adjuvants in vaccines for therapeutic or prophylactic vaccination. In particular, compounds according to the general formula (I) demonstrate the applicability as parenteral adjuvants and, in particular, as mucosal adjuvants.

As used herein, the term "adjuvant" means substances which are added and/or co-formulated in an immunization to the active antigen, i.e. the substance which provokes the desired immune response, in order to enhance or elicit or modulate the humoral and/or cell-mediated (cellular) immune response against the active antigen. Preferably, the adjuvant according to the present invention is also able to enhance or elicit the innate immune response.

The term "therapy" or "treatment" refers to a process that is intended to produce a beneficial change in the condition of an individual like a mammal, e.g., a human, often referred to as a patient, or animal. A beneficial change can, for example, include one or more of: restoration of function, reduction of symptoms, limitation or retardation of progression of a disease, disorder, or condition or prevention, limitation or retardation of deterioration of a patient's condition, disease or disorder. Such therapy usually encompasses the administration of a drug, among others.

As used herein, the term "delivery system" refers to a system that is more inert and has less immunomodulatory effects than adjuvants and which can protect and deliver the vaccine to the site of interest through the site of administration. In particular, the delivery system allows for more efficient presentation of the antigen to the immune system. Examples of delivery systems are virus or virus-like particle, ISCOM, nanoparticles, microparticles, liposomes, virosomes and virus-like particles.

As used herein, the term "pegylated" refers to the conjugation of a compound moiety with conjugate moiety(ies) containing at least one polyalkylene unit. In particular, the term pegylated refers to the conjugation of the compound moiety with a conjugate moiety having at least one polyethylene glycol unit.

As used herein, the term "mucosal" refers to mucosal surface from the body such as the nasal, oral, gastro-enteric, rectal, urinary, conjunctial, glandular, e.g. mammary gland, epithelial mucous.

As used herein, the term "conjugate" refers to compounds comprising a conjugate moiety and a compound moiety. The compound moiety is any one of formula (I). The term "conjugate moiety" refers to a moiety which is linked to the compound according to formula (I). The conjugate moiety aims to increase the applicability of the compounds disclosed herein.

As used herein, the term "antigenic structure" or "antigen" refers to a structure capable of causing a cellular or humoral immune response. The antigenic structure, also known as epitope is the part of the antigen, which is presented by the MHC or MHC like molecules. Further, the epitope or antigenic structure represents the part of an antigen recognized by antibodies directed against said antigen.

As used herein, the term "modulate an immune response" refers to any change of the present state of the immune response. The immune response may be modulated insofar that the response is elicited or a pre-existing immune response is enhanced or decreased. In addition, the immune response may be modulated by shifting the immune response from a more humoral to a more cellular immune response or vice versa. Further, the immune response may be modulated by switching or redirecting the response from a Th1 to Th2 or Th3 response or vice versa or to provide a balanced Th1/Th2 response. In addition, the modulation of the immune response may encompass the activation or enhancement of the innate immune response.

As used herein, the term "individual" or "subject" which is used herein interchangeably refers to an individual or a subject in need of a therapy or prophylaxis. Preferably, the subject or individual is a vertebrate, even more preferred a mammal, particularly preferred a human.

As used herein, the term "carrier" refers to a diluent, adjuvant, excipient, or vehicle. The present invention relates to the use of at least one of the compounds according to formula (I)

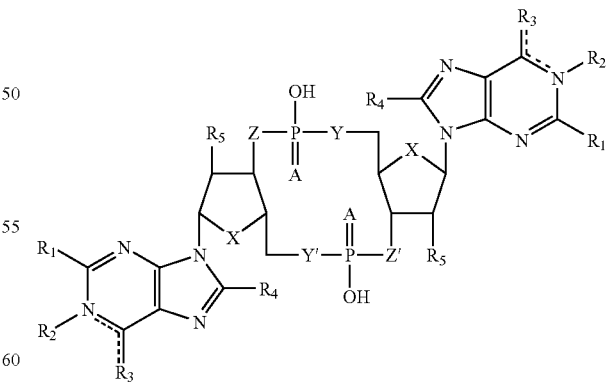

wherein
A is S or O;
X is S, N, O, CH2;
Y, Y' is NH, CH2, O;
Z, Z' is NH, CH2, O;

R1 represents hydrogen or NH2 which may be substituted;

R2 is hydrogen or absent;

R3 represents NH2, O, OH, H, or a halogen;

R4 represents hydrogen, halogen, or a straight or branched C1-C6 alkyl group which may optionally be substituted;

R5 represents hydrogen, OH or a straight or branched C1-C6 alkyl chain or C1-C6 straight or branched alkoxy chain which may optionally be substituted;

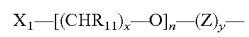 is a single or double bond;

or conjugates thereof, and salts or solvates thereof, as adjuvant(s) for therapeutic or prophylactic vaccination.

In formula (I), the purine residue is preferably a guanine (G), adenine (A), xanthine or hypoxanthine (X), or inosine (I) residue. The compound according to the present invention may have identical purine residues, e.g. c-diGMP, c-diAMP, c-diIMP, or c-dXMP, or may contain different purine residues, e.g. c-GpAp, c-GpIp, c-GpXp, c-ApIp, c-ApXp, or c-IpXp. Further, R5 is preferably an OH group. In addition, X is preferentially an oxygen atom. In a preferred embodiment, Y, Y', Z, and Z' are an oxygen atom, O.

Thus, in a preferred embodiment, the compound of formula (I) is a cyclic bis(3'-5')diguanylic acid (c-diGMP) or conjugates thereof or a cyclic bis(3'-5')diadenylic acid (c-diAMP) or conjugates thereof, or salts or solvates thereof. In the most preferred embodiment, the compound of formula (I) is cyclic Bis(3'-5')adenylic acid, which is also referred to as c-di-AMP in the following, or the pegylated conjugate.

With the term "which may be substituted" is meant the substitution with a straight or branched C1-C6 alkyl group or a straight or branched C1-C6 alkoxy group and/or with a halogen, hydroxyl group or carboxyl group.

The conjugate moiety of the conjugate according to the present invention is a covalently bonded, physiologically tolerated conjugate moiety, which is suitable for converting the compounds according to formula (I) into a more water-soluble form. For example, the conjugate moiety can be a polymer, a dextran, a sugar, a polyvinylpyrrolidone, an alginate, a pectin or collagen. The conjugate moiety is characterized in that is provides good water and is not immunogenic. The conjugate moiety may be covalently bound with the residue.

The conjugate moiety of the conjugate claimed herein, is in a preferred embodiment, a conjugate moiety containing at least one polyalkylene glycol unit of the formula:

$$X_1-[(CHR_{11})_x-O]_n-(Z)_y-$$

where $X_1$ is hydrogen or a hydrocarbon which may contain heteroatom(s); e.g C1-C6 alkoxy group Z is a divalent linkage group, such as C=O or $CHR_{11}$;

$R_{11}$ is independently any one of hydrogen, OH, $OR_{12}$ or $CO-R_{13}$;

$R_{12}$ is independently any one of hydrogen or straight or branched $C_1-C_6$ alkyl chain;

$R_{13}$ is independently any one of hydrogen, OH, $OR_{12}$ or $NR_{14}R_{15}$;

$R_{14}$ and $R_{15}$ are independently any one of hydrogen or hydrocarbon which may contain heteroatom(s) and which may form a ring;

n is an integer of 1 to 100;

x is independently an integer of 1 to 10;

y is an integer of 0 to 10.

Preferably, n is an integer of 2 to 50, like 2 to 10, in particular 3 to 5.

Preferably, x is an integer of 2, 3, or 4, in particular, 2.

y is preferred an integer of 1 to 5, in particular, 1 to 3, in another preferred embodiment, y is 0. $X_1$ is preferentially $OR_{16}$, $N(R_{16})_2$, $SR_{16}$ or $COOR_{16}$, wherein each $R_{16}$ is individually hydrogen, benzyl or straight or branched $C_1-C_6$ alkyl chain. Preferably X1 is a $C_1-C_6$ straight or branched alkoxy group, like a methoxy, ethoxy or propoxy group.

$R_{11}$ is preferably a hydrogen atom.

Thus, the polyalkylene glycol unit mentioned above may preferably contain subunits $-[(CHR_{11})_x-O]_n$ of ethylene glycol, propylene glycol or butylene glycol or combinations thereof. The chain length of each of the polyalkylene glycol units may be in the range of 1 to 100 subunits, preferably, 2 to 50 subunits, like 2 to 10 subunits, particularly in the range of 3 to 5 subunits.

Particularly preferred is the conjugate moiety a methoxy-polyalkyleneglycol-carbonyl-residue wherein the alkylene moiety is an ethylene or propylene moiety.

Hence, preferably the conjugates are in a pegylated form to increase the solubility in hydrophilic solvents and hydrophilic environment. Furthermore, the conjugate moiety allows protecting the compound moiety, i.e. the active mucosal adjuvant moiety, against enzymatic degradation, structural modification due to change of the pH, mechanical removal, etc. Thus, primarily the stability of the compound is increased. Another beneficial effect of conjugation is to increase the retention time in the individual, e.g. to delay the renal excretion, while being well-tolerated, e.g. being non immunogenic, by said organism. Further, the conjugates, in particular pegylated conjugates improve the bioavailability of the compounds and allow to reduce the dosage administered to the individual.

Specifically, the conjugate moiety comprises at least two chains having polyalkylene glycol units. That is, the conjugate may be a branched compound wherein each arm contains a polyalkylene glycol unit. Particularly preferred are conjugate moieties wherein the polyalkylene glycol unit is a polyethylene, polypropylene or polybutylene glycol unit.

In a particularly preferred embodiment, the compound moiety according to formula (I) is covalently linked with the conjugate moiety being a branched moiety wherein at least two arms containing polyethylene glycol units having 3 to 5 ethylene glycol subunits and a methoxy group at the free end of the polyethylene group. In particular, the branched moiety comprises 4 or 6 arms each having 3 ethylene glycol subunits and a methoxy group at the free end of the polyethylene group.

In particular, the conjugate is characterized in that the conjugate moiety is 4armPEG ((S)-10-Amino-6,9,13,16-tetraoxo-N,N',8,14-tetrakis(3,6,9,12-tetraoxatridec-1-yl)-5,8,14,17-tetraazahenicosane-1,21-diamide),6armPEG or 8armPEG, see also http://ww.celares.com. Other suitable conjugate moiety comprising at least one polyethylene unit are obtainable e.g. from celares GmbH, Berlin, see http://www.celares.com.

In another embodiment of the present invention, the conjugate moiety comprising a polyalkylene glycol unit is a linking group linking two or more of the cyclic dinucleotide compounds according to the present invention. Preferably, the polyalkylene glycol unit is a polyethylene unit containing 2 to 20 ethylene glycol subunits, e.g. 4, 6, 8, 10 or 12 subunits. Such molecules are exemplified in FIG. 13.

The compounds of formula (I) or conjugates thereof may be in the form of pharmaceutically acceptable non-toxic salts thereof. Salts of formula (I) include acid added salts, such as salts with inorganic acids (e.g. hydrochloric acid, sulphuric acid, nitric acid and phosphoric acid) or with organic acids (e.g. acetic acid, propionic acid, maleic acid, olec acid, palmitic acid, citric acid, succinic acid, tartaric acid, fumaric acid, glutamic acid, panthothenic acid, laurylsulfonic acid, methanesulfonic acid and phthalic acid).

The compounds of formula (I) or conjugates thereof may be in the form of solvates thereof (e.g., hydrates).

In addition, the compounds of formula (I) may form salts with cationic ions, like metallic ions, in particular alkali or alkaline earth metal ions, or NH4+.

The compounds according to formula (I) can be synthesized by known methods, e.g. as described in Somanathan, R., et al, 1981, J Heterocyclic Chem, 18, 1077 and Hyodo, M., et al 2004, Bull. Chem. Soc. Jpn, 77, 2089 which are incorporated herein by reference.

The synthesis of conjugates may be conducted by methods known to the person in the art. For example, a hydroxyl group may be converted into a halogen residue, e.g. Cl. Br, I and this residue can react with modified conjugates having a free amino-group. For example, synthesis of pegylated conjugates are described in Veronese F. M., Biomaterials 22 (2001), 405-417 and Kodera Y., et al., Prog. Polym. Sci. (1998), 23,1233-1271 which are incorporated herein by reference.

In a preferred embodiment, the compound(s) or conjugate(s) according to formula (I), their conjugates or salts or solvates thereof are useful as mucosal adjuvant(s), in particular, for intranasal, intra NALT, oral, intra-rectal, conjunctival, intra-vaginal, intrathecal, intrabronchial, intrapulmonary, or intra-urethral administration, administration into the milk ducts of the breast or by inhalation.

Particularly preferred is the intranasal administration or the administration by inhalation using suitable aerosol formulations. Aerosol formulations useful for administration of vaccines are known in the art.

The compounds according to formula (I), their conjugates or salts or solvates thereof are also suitable as systemic adjuvant(s). Thus, the adjuvants described herein are also applicable as parenteral adjuvant(s), in particular, in subcutaneous, intravenous, intradermal, topical or intramuscular administration.

The adjuvant of the invention can be linked by all methods known to the skilled person to the antigen or active molecule intended for the vaccination, be incorporated together with the latter in physical (e.g. microparticles, nanoparticles, liposomes, ISCOMS, polymers) or biological particles (bacteria, bacterial parts) or virosomes or be mixed with the antigen. For example, the adjuvant may be co-formulated or admixed with the antigen. For binding to carriers it is also possible to provide transport molecules or transport proteins as carriers.

The compound(s) according to the formula (I), their conjugate(s) or salts or solvates thereof is/are preferably present in a preparation with the active vaccination component (e.g. the antigen) which is suitable and provided for intranasal, intra-NALT (nasal associated lymphoid tissue), aerosolized, oral, intrarectal, conjunctival, intravaginal, intraurethral administration or for administration into the milk ducts of the breast. Particularly, the preparation is provided in formulation suitable to be taken up via the respiratory tract or the gastrointestinal tract. Alternatively, the mucosal adjuvant of the invention can be present in a kit for co-administration with a vaccine by one of the aforementioned routes and be adapted therefore where appropriate. That is the vaccine may be administered simultaneously, sequentially or separately with the active vaccination component.

The compounds and its conjugates according to the present invention direct the immune response towards a balanced Th1/Th2 immune response which is demonstrated by enhanced IFNy for Th1 cytokines and IL-4 for Th2 cytokines.

In another embodiment, the present invention relates to methods of treating individuals afflicted with a disease or condition that can be treated by modulating the immune response comprising administering to said individual an effective amount of a pharmaceutical comprising the compounds according to formula (I) or their conjugates, salts and solvates thereof as defined herein as an adjuvant, particularly as a mucosal adjuvants together with an active vaccination component, and, optionally, a pharmaceutically acceptable carrier.

Preferably, the method relates to the treatment of individuals afflicted with an infectious disease wherein the infectious disease is produced by an infectious agent selected among those causing human or animal disease at the level of the respiratory tract, gastrointestinal tract, genitourinary tract, osteoarticular system, skin or mucosa.

The compounds or conjugates or salts or solvates thereof as defined herein are particular useful as mucosal adjuvants for activating or enhancing in vitro and/or in vivo the antigen presenting function of antigen presenting cells for a therapeutic or prophylactic intervention. That means, the adjuvants can stimulate macrophages, can stimulate or enhance the humoral immune response, e.g. enhancing or stimulating the production of antibodies. In addition, the adjuvants can also enhance or stimulate the cellular immune response, e.g. increasing the proliferation of T-cells. In addition, it is possible to use the adjuvant(s) for ex vivo stimulation in cell culture, e.g. for the production of dendritic cells, etc. These cells obtained by ex vivo stimulation may be used for autologous cell transfer in transplantation or as a cell based vaccine against diseases or conditions, like the diseases and conditions mentioned above, including cancer, autoimmune disease or allergies.

Thus, in case of the use of the compounds or conjugates or salts or solvates thereof as defined herein as an adjuvant, the pharmaceutical composition according to the present invention is preferably a vaccine, comprising said compounds or conjugates or salts or solvates thereof as pharmaceutically acceptable adjuvant(s) together with the active vaccination component (e.g. the antigen) and, optionally, a pharmaceutically acceptable carrier, diluent, preservative, adjuvant other than the adjuvant according to the present invention, immunomodulator or excipient.

The active vaccination component may be any component suitable to elicit, enhance or modulate an immune response in an individual. The active vaccination component is suitable particularly for intranasal, intra-NALT, oral, intrarectal, conjunctival, intra-vaginal, aerosolized or intra-urethral administration, or administration into the milk ducts of the breast.

For example, the active vaccination component, the active ingredient of the pharmaceutical composition, comprises at least one or more different antigens in the form of peptides, proteins, polysaccharides, glycolipids or DNA encoding them or bacterial ghost, virosomes, or attenuated vaccines.

Preferentially, the antigen(s) are tumor antigen(s) or antigen(s) derived from infectious agents. The infectious agents include those agents which normally enters individual's organism by crossing the mucous membrane.

The pharmaceutical composition comprising adjuvant(s) according to the present invention, an active vaccination component, optionally additional carrier, diluent, preservative, adjuvant other than the adjuvant according to the present invention, immunomodulator or excipient may additionally contains components, like compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

However, the compounds according to formula (I), their conjugates salts and solvates thereof as defined herein for the use as adjuvants may also be a component of a pharmaceutical composition provided in a formulation suitable for parenteral administration, in particular, in subcutaneous, intravenous, intradermal or intramuscular administration.

Further, the compounds and conjugates according to the present invention are useful in tumor therapy including the in vitro generation or in vitro priming of autologous cells for adoptive cell transfer in tumor therapy and transplantation. Moreover, the adjuvants are useful for the induction of cross-tolerance against microbial components, like endotoxins, to protect against septic shock or other severe forms of diseases induced by microbial components.

In addition, the compounds and conjugates themselves as defined herein may display a pharmaceutical activity, e.g. are to be useful in the prophylaxis and treatment of various diseases and conditions, like cancer, infectious diseases, septic shock, chronic and inflammatory processes, autoimmune diseases, allergies, etc.

Hence, the compounds according to formula (I), their conjugates or salts or solvates thereof are also useful for the preparation of a pharmaceutical to prevent or treat infectious diseases, septic shock, cancer, tumors, autoimmune diseases, allergies, or chronic or acute inflammatory processes.

The conjugates according to the present invention and salts or solvates thereof, particularly, the pegylated conjugates, can be used as active ingredients in pharmaceuticals useful for the prevention or treatment of infectious diseases, septic shock, tumors, autoimmune diseases, allergies, or chronic or acute inflammatory processes. In particular, the conjugates or salts or solvates thereof are contained in pharmaceuticals useful for preventing or treating cancer and/or tumors, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, helicobacter pylori, herpes virus, etc.; bacterial infections, such as tuberculosis, leprosy and listeriosis, and parasitic infections such as malaria.

Thus, in a further aspect, the present invention relates to pharmaceutical compositions comprising conjugates according to formula (I) or salts or solvates thereof, in particular, conjugates containing at least one conjugate moiety comprising a polyalkylene glycol unit, as defined herein or salts or solvates thereof and, optionally, a pharmaceutically acceptable carrier. Such pharmaceutical compositions comprise a therapeutically effective amount of the conjugates and, optionally, a pharmaceutically acceptable carrier. The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin ($18^{th}$ ed., Mack Publishing Co., Easton, Pa. (1990)). Such compositions will contain a therapeutically effective amount of the aforementioned conjugates containing compounds according to formula (I), salts or solvates thereof, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will typically involve an increase in the immunological responses to infection or a suppression of the responses to inflammatory processes.

In vitro assays may optionally be employed to help identifying optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. Preferably, the pharmaceutical composition is administered directly or in combination with an adjuvant.

The term "administered" means administration of a therapeutically effective dose of the aforementioned pharmaceutical composition comprising the conjugates containing the compound according to formula (I), salts and solvates thereof as defined herein to an individual. By "therapeutically effective amount" is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In still another embodiment, the present invention relates to methods of treating individuals suffering from infectious diseases, septic shock, tumors, autoimmune diseases, allergies, or chronic or acute inflammatory processes comprising the step of administering to said individual an effective amount of a pharmaceutical comprising a conjugate according to formula (I) or salts or solvates thereof as the active ingredient, and, optionally, a pharmaceutically acceptable carrier. In particular, the method is useful for preventing or treating cancer and/or tumors, such as, melanoma, prostate, breast, colorectal, stomach, throat and neck, pancreatic, cervical, ovarian, bone, leukemia and lung cancer; viral infections, such as, hepatitis B, hepatitis C, human immunodeficiency virus, helicobacter pylori, herpes virus, etc.; bacterial infections, such as tuberculosis, leprosy and listeriosis, and parasitic infections such as malaria.

Further, the pharmaceutical composition may contain additionally components, e.g. compounds like one or more anti-inflammatory molecules, anti-angiogenic molecules, cytotoxic molecules, immunomodulatory molecules, preferably chemokines, cytokines, CD40 ligand, costimulatory molecules or antibodies or mixtures thereof.

In addition, the pharmaceutical composition described herein may be characterized in that the components of the pharmaceutical composition are associated and/or incorporated and/or coated to a physical particle, preferably microparticle, nanoparticle, liposome, ISCOM, copolymer and/or biological particle, preferably bacterial ghosts.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intra-arterial, intranodal, intramedullary, intrathecal, intraventricular, intranasally, conjunctival, intrabronchial, transdermally, intrarectally, intraperitoneally, intramuscularly, intrapulmonary, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 1000 μg; however, doses below or above this exemplary range are envisioned, especially considering the aforementioned factors.

In still another aspect, the present invention relates to the use of the compound(s). or salts or solvates thereof as defined herein in a pharmaceutical preparation to control fertility in human or animal populations.

Finally, the present invention relates to kits comprising the compounds or conjugates according to the present invention or salts or solvates thereof. In particular, the kit is useful for the preparation of pharmaceutical compositions. Optionally, the kit contains instructions for preparing the pharmaceutical composition.

In a preferred embodiment thereof, the kit contains the compound or conjugate according to the present invention or salts or solvates thereof as an adjuvant and an antigen comprising an antigenic structure and, optionally, a pharmaceutically acceptable carrier, diluent, preservative, adjuvants other than the conjugates according to the present invention, immunomodulators or excipient and instructions for preparing a vaccine.

These and other embodiments are disclosed and encompassed by the description and examples of the present invention. Further literature concerning any one of the methods, uses and compounds to be employed in accordance with the present invention may be retrieved from public libraries, using for example electronic devices. For example the public database "Medline" may be utilized which is available on the Internet, for example under http://www.ncbi.nlm.nih.gov/PubMed/medline.html. Further databases and addresses, such as http://www.ncbi.nlm.nih.gov/, http://www.infobiogen.fr/, hftp://www.tigr.orq/, are known to the person skilled in the art and can also be obtained using, e.g., http://www.google.de. An overview of patent information in biotechnology and a survey of relevant sources of patent information useful for retrospective searching and for current awareness is given in Berks, TIBTECH 12 (1994), 352-364.

BRIEF DESCRIPTION OF THE FIGURES

FIG. 1 shows the cytometric determination of the CD40 co-stimulatory molecule on the surface of murine dendritic cells after stimulation with c-diGMP and without any stimulus.

FIG. 2 shows a comparison of antibody expression of β-gal specific IgG titer in sera. Intranasal administration of antigen with c-diGMP results in increased expression of β-gal specific IgG antibodies.

FIG. 3 represents the humoral responses stimulated in mice vaccinated using c-diAMP as adjuvant. Kinetic analysis of anti-beta-Gal IgG responses from mice (n=5) immunized on day 1, 14, and 28 with PBS (negative control), beta Gal (30 μg/dose) or beta-Gal co-administered with c-diAMP (10 μg/dose) by the i.n. or s.c. route. One representative out of three independent experiments is shown.

FIG. 4 demonstrates higher β-gal specific IgA expression in lung lavage of β-gal/c-diGMP immunized mice than in mice which received β-gal only.

FIG. 5 shows an analysis of antigen-specific IgA in lung and vaginal lavages for the groups immunized with PBS, beta-Gal and beta-Gal+c-diAMP, respectively, in mice immunized by the i.n. route. Results are expressed as beta-Gal specific IgA titers with respect to 1 μg total IgA in BAL or VL. SEM is indicated by vertical lines. Differences were statistically significant at p<0,05 (*) with respect to mice receiving antigen alone. One representative out of three independent experiments is shown.

FIG. 6 illustrates that c-diGMP and c-diAMP are efficient adjuvants for the stimulation of spleen cells in i.n. and s.c. vaccination. FIG. 6 shows the proliferative responses stimulated in mice using c-diAMP as adjuvant. Results in c-diGMP are averages of triplicates and are expressed as (A) counts per minute (cpm) or (B) stimulation index (SI). The results in c-diAMP vaccinated animals, expressed as (C) counts per minute (cpm) or (D) stimulation index (SI), were statistically significant with respect to those observed in mice receiving beta Gal alone at p<0,05 (*). One representative out of four independent experiments is shown.

FIG. 7 demonstrates the strong expression of Th1 cytokines like IFNg in restimulated cells immunized with antigen and c-diGMP FIG. 8 illustrates that.Th1 like cytokines are expressed in antigen restimulated cells when using c-diAMP as an adjuvant. (A) shows unstimulated spleen cells and (B) demonstrates that high expression of Th1 like cytokines can be observed in mice received β-gal/c-diGMP in contrast to mice which received β-gal alone FIG. 9. shows the secretion of Th1/Th2 cytokines of mice being immunized i.n. or s.c., respectively. The supernatants were analysed for the contents of IFNγ, TNFα, IL-12, IL-6, MCP-1 and IL-10 by cytometric bead array. Differences were statistically significant at p<0,05 (*) with respect to mice receiving antigen alone. One representative out of three independent experiments is shown.

FIG. 10 illustrates that. c-diGMP (A and B) and c-diAMP (C) and (D) administered as an adjuvant provides increased expression of various cytokines.

FIG. 11 shows the analysis of beta-Gal specific IgG titers in sera of immunized mice. Anti-beta-Gal-specific IgG titers of the groups immunized with PBS, beta-Gal+c-diAMP (10 μg) or beta-Gal alone of mice immunized by the i.n. (A) or s.c. (B) route were determined by ELISA. Results are expressed as end point titers. IgG titers represent the mean of five animals per experimental group. Differences were statistically significant at p<0,05 (*) with respect to mice receiving antigen alone. One representative out o f four independent experiments is shown. SEM is indicated by vertical lines.

FIG. 12 provides the analysis of beta-Gal specific IgG isotypes in sera of immunized mice. Anti-beta-Gal specific IgG isotypes of the groups immunized with PBS, beta-Gal+c-diAMP (1 and 5 μg) or beta-Gal alone of mice immunized by the i.n. (A) or s.c. (B) route were determined by ELISA. Results are expressed as end point titers. IgG titers represent the mean of five animals per experimental group. Differences were statistically significant at p<0,05 (*) with respect to mice receiving antigen alone. One representative out of four independent experiments is shown. SEM is indicated by vertical lines.

FIG. 13: FIG. 13 shows another embodiments of the compounds according to the present invention whereby two cyclic dinucleotides are covalently linked with each other via a polyethylene glycol unit. Compound 13a having 4 ethyleneoxide units and compound 13b having 12 ethyleneoxide units.

EXAMPLES

1. In Vitro Stimulation of Primary Bone Marrow-Derived Murine Dendritic Cells with c-diGMP Experimental protocol: primary bone marrow-derived dendritic cell cultures were obtained from BALB/c mice following in vitro maturation of precursors in the presence of recombinant GM-CSF ($5 \times 10^4$ U/ml), according to established protocols, e.g. Link, C., etal, 2004, Eur. J. Immuol, 34(3):899-907. Mature dendritic cells were stimulated with 10 ng/ml of *E. coli* lypopolysaccharide (LPS) or 10 ng/ml c-diGMP. The stimulation of cells was analyzed by flow cytometry to assess the expression of surface markers which are relevant for their antigen presentation capacity after 12 h and 24 h, respectively.

In order to identify compounds which may have potential as adjuvants for in vivo applications in the field of vaccines, a first in vitro screening based on the use of primary cultures of bone marrow-derived dendritic cells was established. Dendritic cells were selected since they represent the most efficient antigen presenting cells and they play a key role in primary immune responses. In fact, they represent the only cell type able to activate resting T cells initiating primary immune responses in vivo. Thus, dendritic cell cultures were treated with the tested title compounds or LPS, which was used as a positive control. At different time intervals, samples were taken, stained with fluorescent-labeled antibodies specific for cellular markers critical for the antigen presenting capacities of dendritic cells, and analyzed by flow cytometry.

Figure 1:
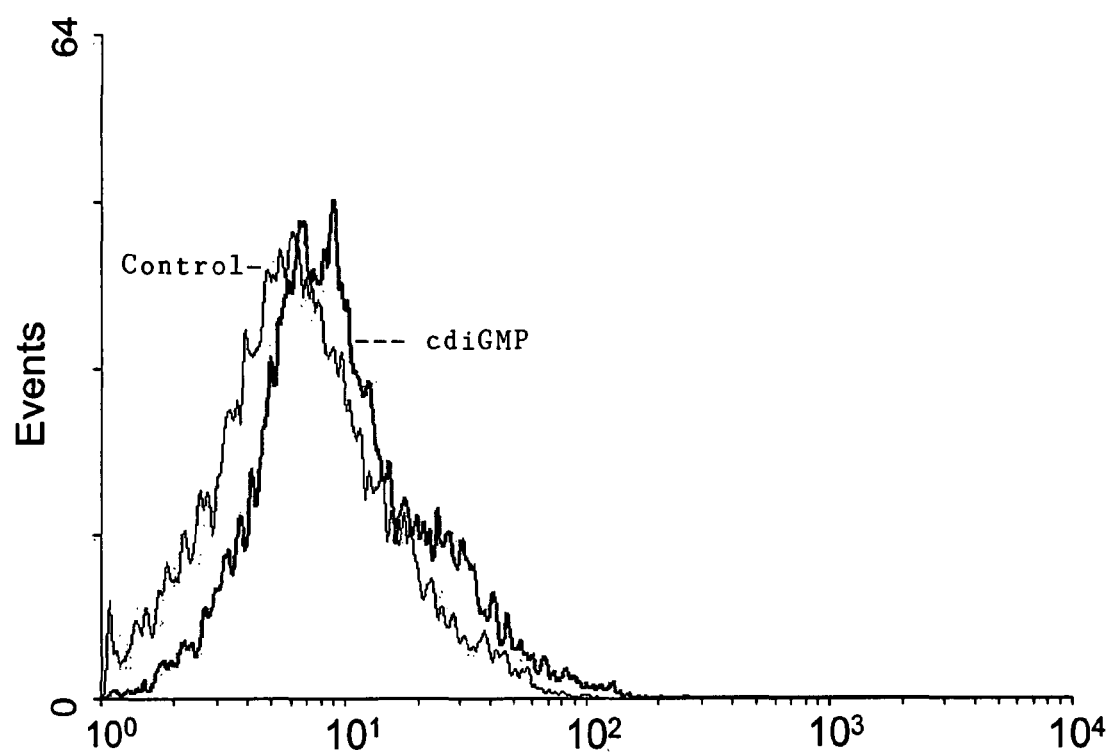
FIG. 1.

The obtained results (FIG. 1) demonstrated that in contrast to the control, group which received no c-diGMP, the expression of CD40 was up-regulated in the c-diGMP treated dendritic cells. Co-stimulatory molecules deliver signals which are essential for the efficient activation of T cells in addition to the presentation of the processed epitopes in the context of the MHC class II molecules. It has been previously reported that the adjuvanticity of well-established mucosal adjuvants, such as cholera toxin, involves the selective up-regulation of the expression of co-stimulatory molecules. Thus, these in vitro results strongly argue for a high potential of c-diGMP as mucosal adjuvants.

Figure 2:
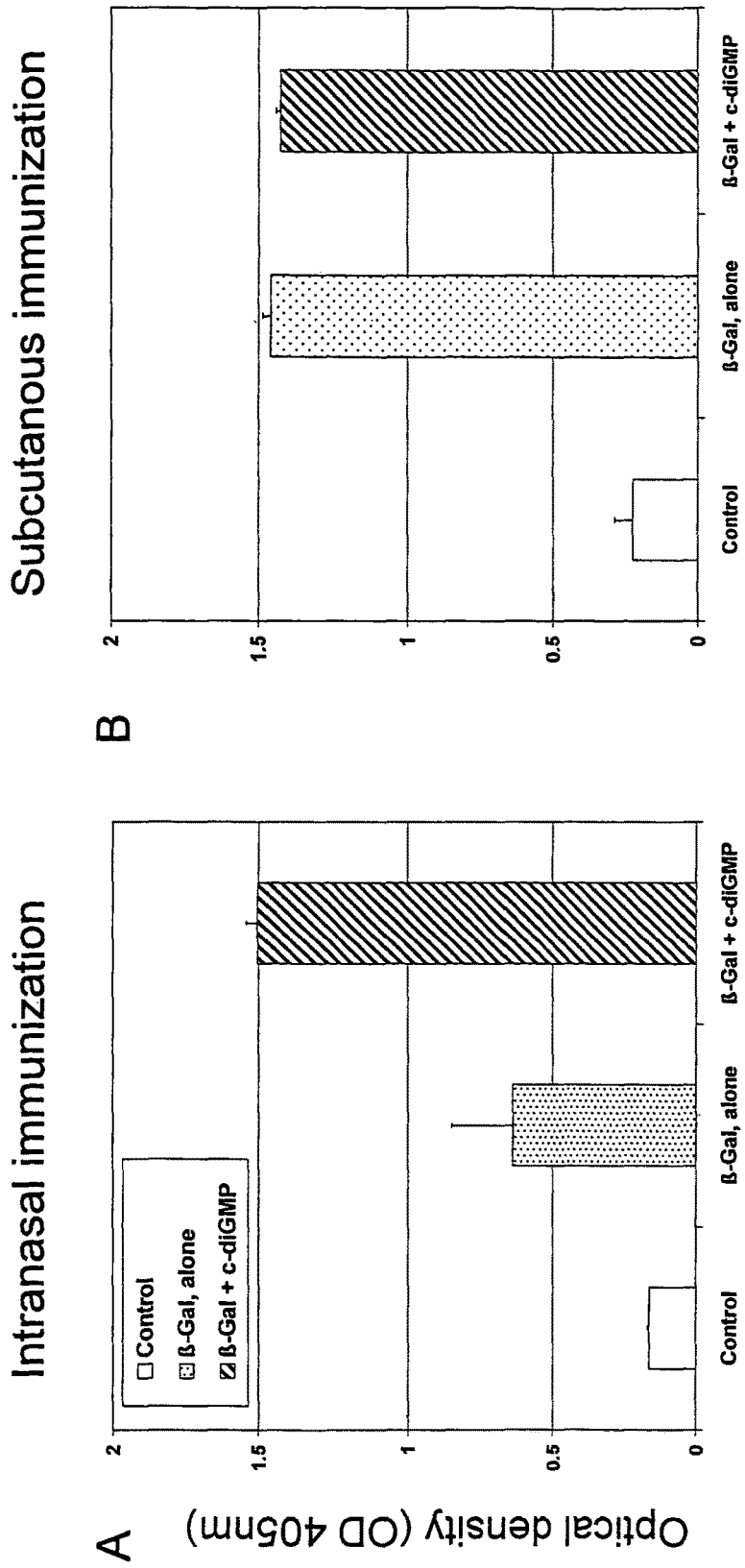
FIG. 2.
Figure 3:
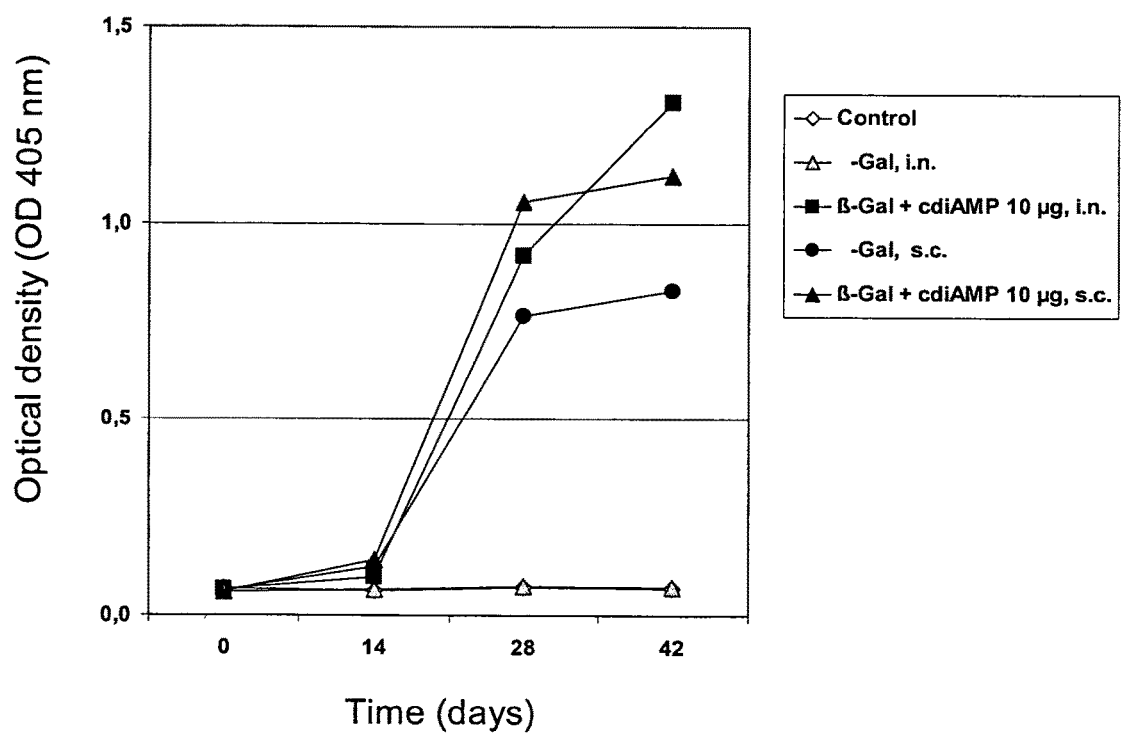
FIG. 3.

2. Intranasal and Intraperitoneal Co-Administration of c-diGMP and c-diAMP with a Soluble Antigen Stimulates Efficient Systemic Humoral Responses Experimental protocol: six-eight weeks-old female BALB/c (H-2d) mice were purchased from Harlan Winkelmann GmbH (Borchen, Germany) and treated in accordance with local and European Community guidelines. Groups of 5 mice each were immunized on day 1, 14 and 28 with 30 μg of β-gal (Boehringer, Mannheim, Germany), alone or as an admixture with 10 μg c-diGMP or with 10 μpg c-diAMP. For intranasal (i.n.) immunization, 10 μl were applied to each naris, whereas for the s.c. injection β-gal with or without c-diGMP or c-diAMP was resuspended in a volume of 20 μl PBS per animal. Serum samples were collected at day 38 after immunization and stored at −20° C. prior to determination of β-gal-specific antibodies. 96-well Nunc-Immuno MaxiSorp assay plates (Nunc, Roskilde, Denmark) were coated with 100 μl of β-gal (Boehringer, Mannheim, Germany) at 5 μg/ml in 0.05 M carbonate buffer (pH 8.2) per well. Serial two-fold dilutions of sera in PBS with 1% BSA and 0.05% Tween 20 were added (100 μl/well), and plates incubated for 16h at 37° C. After washing, biotinylated γ-chain-specific goat anti-mouse IgG (Sigma Chemie, Deisenhofen, Germany) was added, and plates were incubated for an additional 1 h at 37° C. After four washes, 100 μl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. Results for c-diGMP are shown as OD405 values after serial two-fold dilutions (FIG. 2). As demonstrated in FIG. 2, the IgG-titer was remarkably increased when using c-diGMP. The effect of c-diGMP as an adjuvant was independent of the route of administration. The same can be seen using c-diAMP as an adjuvant, see FIG. 3.

Figure 11:
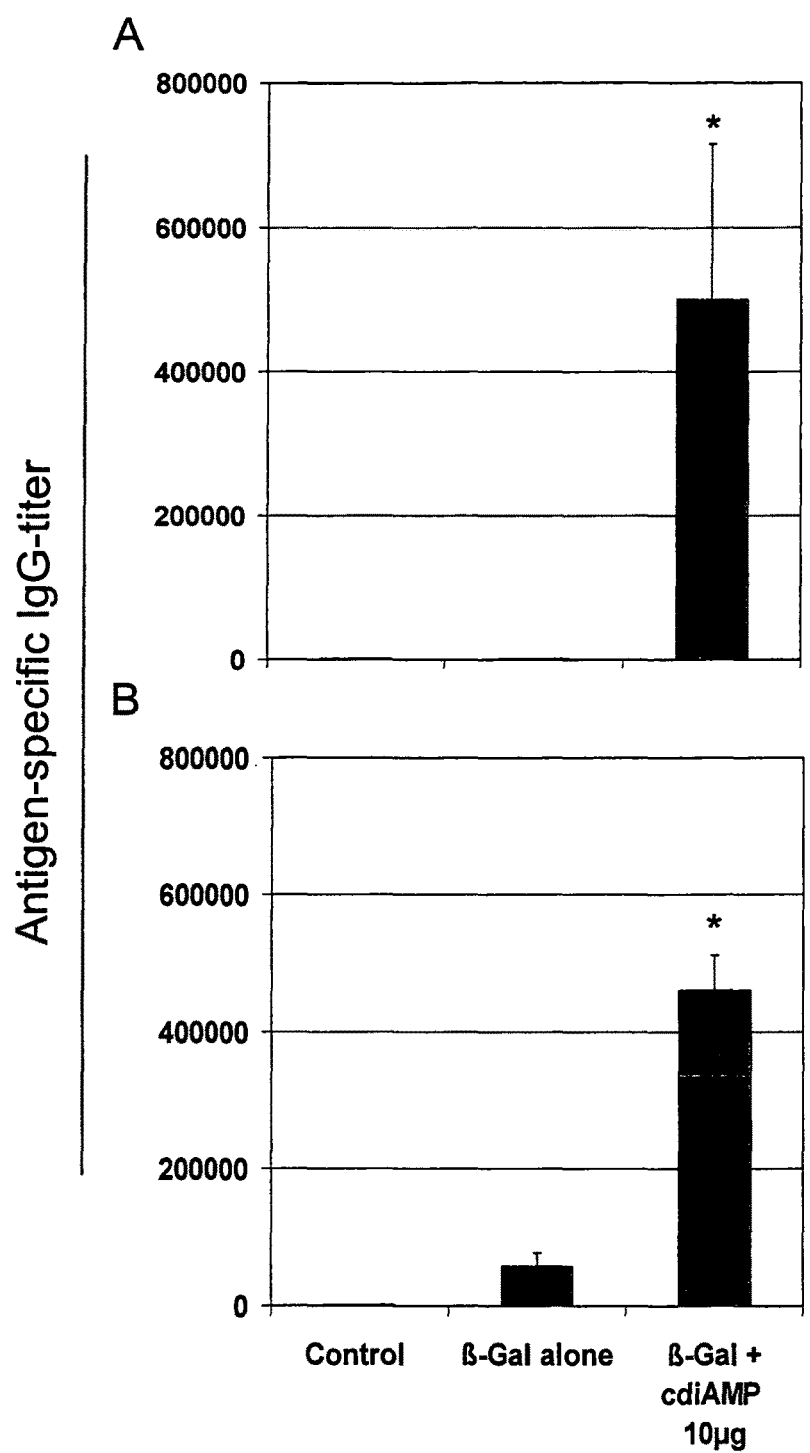
FIG. 11.

Considering the encouraging results obtained in the preliminary studies, it was decided to analyze in detail the immune responses obtained by stimulating with c-diAMP as adjuvant by the two most effective routes, namely s.c. and i.n. Thus, the capacity of c-diAMP to stimulate efficient humoral immune responses was evaluated, by determining the serum titers of β-gal-specific antibodies in vaccinated mice. As shown in FIG. 11, i.n. administration of β-gal alone (30 μg/dose) resulted in the induction of very low antibody titers. In contrast, in the presence of c-diAMP, i.n. administration of β-gal induced very high titers of specific IgG in all mice with titers higher than 500,000 (FIG. 11).

In view of the above in vitro results, additional in vivo studies have been conducted. In detail, the immune responses using β-gal alone or as an admixture with c-diGMP and c-diAMP, respectively, as adjuvant applied by the two most effective routes, namely s.c. and i.n. were determined. Thus, the capacity of c-diGMP and c-diAMP, respectively, to stimulate efficient humoral immune responses was evaluated, by determining the serum titers of β-gal-specific antibodies in vaccinated mice.

3. Intranasal Co-Administration of c-diGMP or c-diAMP with a Soluble Antigen Stimulate Efficient Mucosal Antibody Responses Experimental protocol: at day 38, mice were sacrificed and the final sampling was performed. Vaginal and lung lavages were obtained by flushing the organs with 1 ml of PBS supplemented with 50 mM EDTA, 0.1% BSA, and 10 mM PMSF. Lavages were then centrifuged to remove debris (10 min at 3000×g), and supernatant fluids were stored at −20° C. To determine the concentration of total IgA present in the lung and vaginal lavages, serial dilutions of the corresponding samples were incubated in microtiter plates that were previously coated with goat anti-mouse IgA (Sigma Chemie), as capture antibodies (100 μl/well). Serial dilutions of purified mouse IgA (Sigma Chemie) were used to generate a standard curve.

Figure 4:
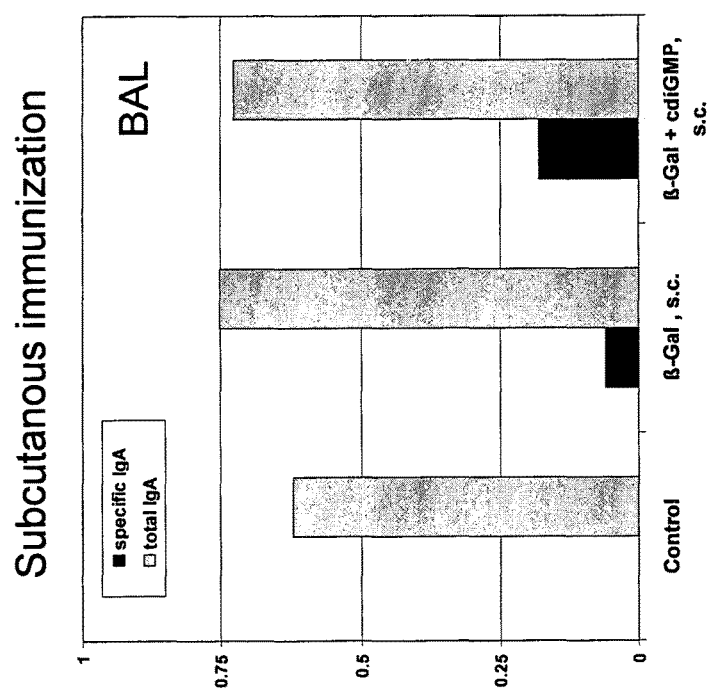
FIG. 4.
Figure 5:
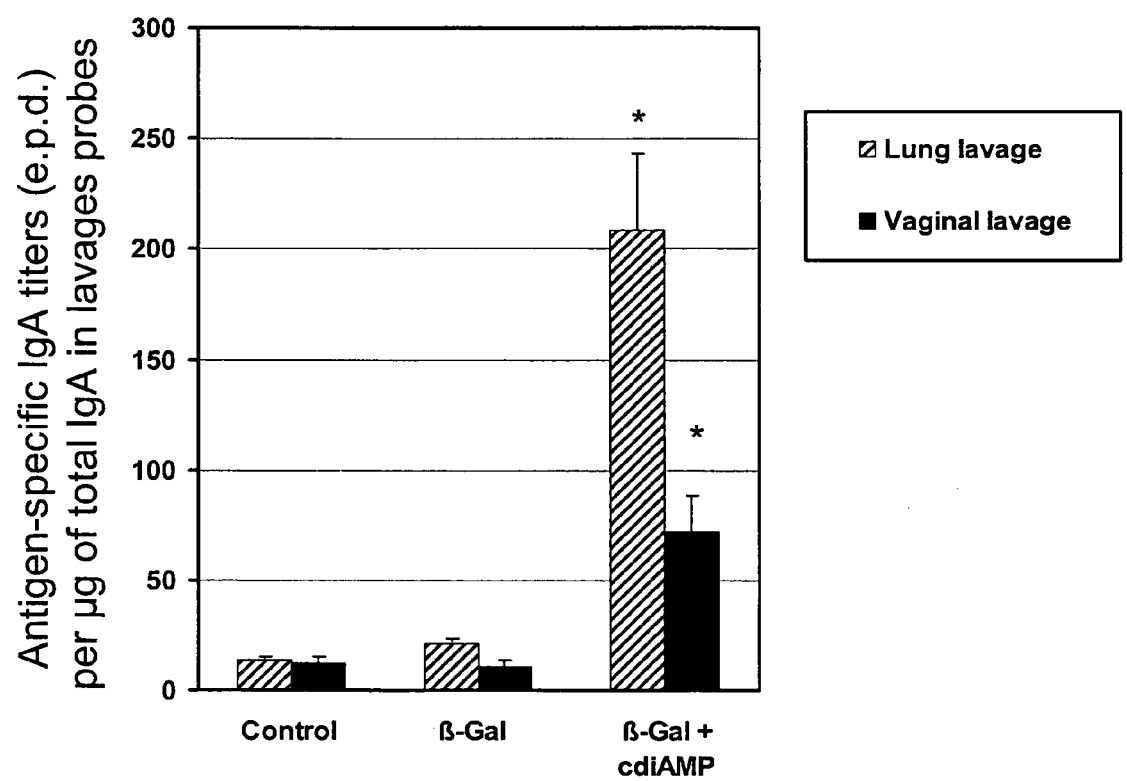
FIG. 5.

To investigate the capacity of c-diGMP and c-diAMP, respectively, to stimulate mucosal responses against antigens co-administered by the i.n. and s.c. route, the production of β-gal-specific IgA in lung was analyzed (FIG. 5 for c-diAMP and FIG. 4 for c-diGMP) from immunized animals, immunized according to the protocol described in Example 2. While i.n. immunization with β-gal alone resulted in a weak production of detectable levels of β-gal-specific IgA in lung lavages, a significant increase in the levels of antigen-specific IgA was detected in animals immunized with β-gal and c-dGMP (FIG. 4) and c-diAMP (FIG. 5). Further, in vaginal lavage β-gal specific sIgA expression is detectable using c-diAMP as an adjuvant (FIG. 5) while c-diGMP does not lead to an enhanced expression of specific sIgA in the vaginal lavage by the s.c. route (not shown).

4. c-diGMP and c-diAMP Stimulate Efficiently T Cell-Mediated Proliferative Responses when Co-Administered with Soluble Antigens Experimental protocol: Spleens were removed and pooled for analysis of cellular immune responses. Cells were grown in RPMI 1640 supplemented with 10% fetal calf serum, 100 U/ml of penicillin, 50 μg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Spleen cell suspensions were adjusted to $5 \times 10^6$ cells/ml in complete medium, cells were seeded with 100 μl per well in a flat-bottomed 96-well microtiter plate (Nunc) and plates were incubated for 4 days in the presence of different concentrations of soluble β-gal. That is, T cell mediated immune responses were investigated at day 38 by measuring the proliferation after in vitro restimulation with β-Gal of cells which have been recovered from spleens before. Said spleen cells were obtained from vaccinated mice—said mice where immunized as described in Example 2—and incubated in the presence of different concentrations of the soluble β-Gal antigen. Each concentration was tested in quadruplicates. During the final 18 h of culture, 1 μCi of [3H]thymidine (Amersham International, Freiburg, Germany) was added to each well. Cells were then harvested on paper filters (Filtermat A; Wallac, Freiburg, Germany) by using a cell harvester (Inotech, Wohlen, Switzerland), and the amount of incorporated [3H]thymidine into the DNA of proliferating cells was determined by a β-scintillation counter (Wallac 1450, Micro-Trilux). The results are expressed as the arithmetic mean of [$^3$H]thymidine uptake in cpm.

Figure 6:
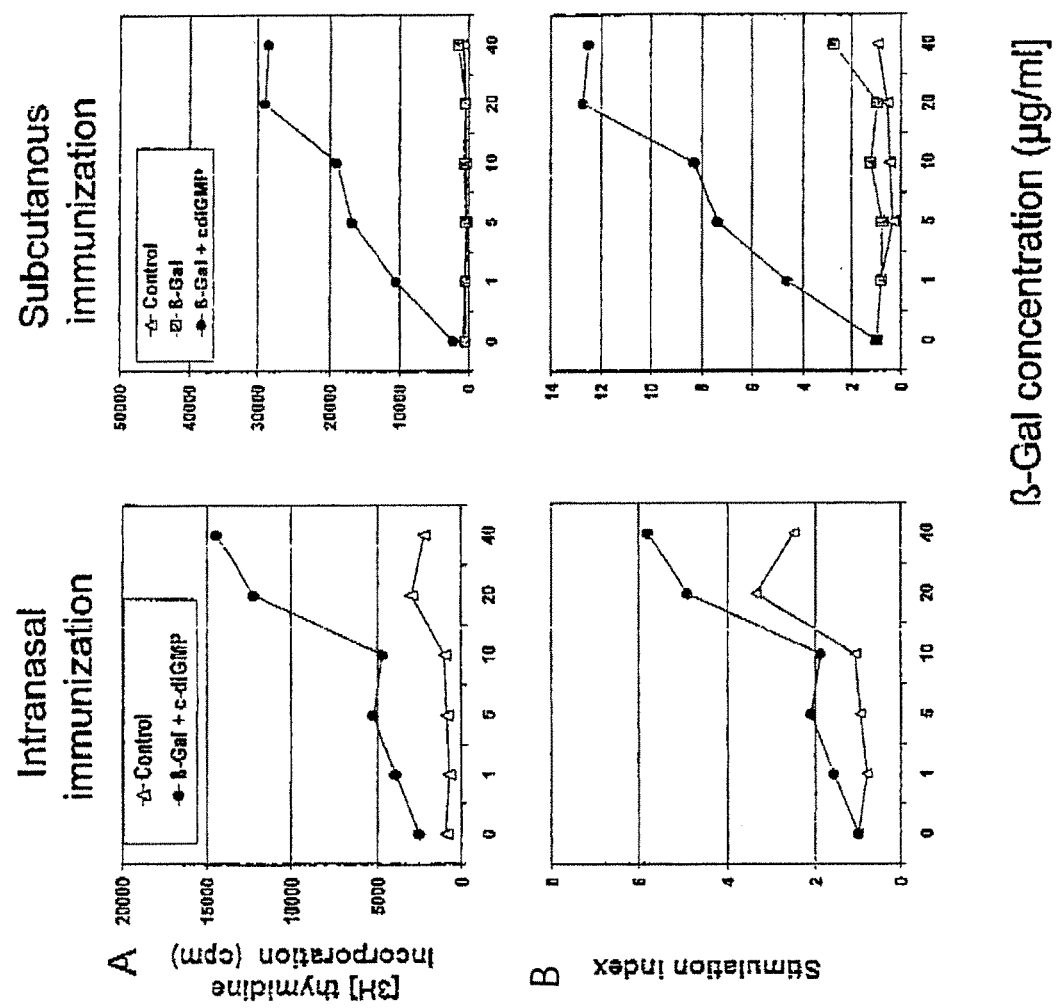
FIG. 6.
Figure 6:
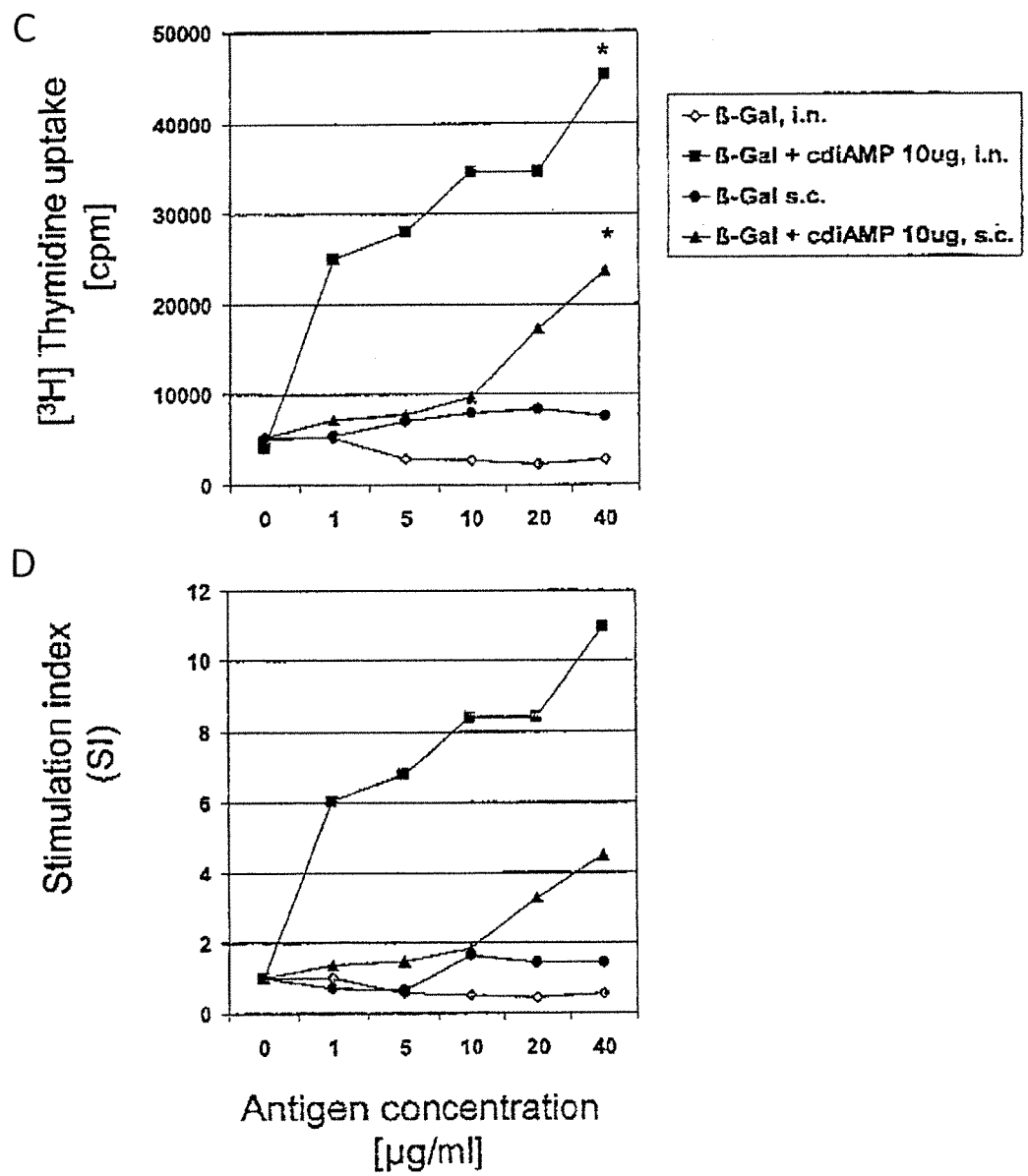

Thirty eight days following vaccination, spleens cells were purified, re-stimulated in vitro in the presence of various amounts of β-galactosidase and their proliferative capacity was estimated by measuring the incorporation of [3H]thymidine into their DNA using a β-scintillation counter. Spleen cells from animals immunized by s.c. injection of β-gal alone, which were chosen as a control, exhibited a significant proliferative response as compared to the non immunized group (FIG. 6 A/B for c-diGMP, FIG. 6C/D for c-diAMP). A further increase in proliferation was noted in spleen cells from animals co-administrated with c-diGMP and c-diAMP, respectively, and antigen. While i.n. administration of β-gal alone failed to induce detectable cellular proliferation, co-administration of c-diGMP and c-diAMP, respectively, triggered the induction of an efficient proliferative response at low amounts of antigen (see FIG. 6).

Of note, the T cell proliferative response was observed with spleen cells of mice immunized with c-diGMP and c-diAMP, respectively, and β-gal administered by the i.n. and the s.c. route, respectively (see FIG. 6).

In all cases a dose dependent effect was observed when increasing the concentration of β-gal in the re-stimulation experiment. Thus, the use of the new adjuvants c-diGMP and c-diAMP, respectively, resulted in a statistically significant increment of the T cell proliferation after i.n. and s.c. administration. These results demonstrate that c-diGMP and c-diAMP, respectively, can increase the cellular immune response.

In addition, the results confirm that other purine based cyclic dinucleotides display the same effect.

5. Analysis of the T Helper Patterns Stimulated by Using c-diGMP and c-diAMP, Respectively, as Adjuvant Isotyp ELISA: 96-well Nunc-Immuno MaxiSorp assay plates (Nunc, Roskilde, Denmark) were coated with 100 µl of β-gal (Boehringer, Mannheim, Germany) at 5 µg/ml in 0.05 M carbonate buffer (pH 9,6) per well. Serial two-fold dilutions of sera or lavages in PBS with 1% BSA and 0.05% Tween 20 were added (100 µl/well), and plates incubated for 2 h at 37° C. After washing, biotin-conjugated rat anti-mouse IgG1 or IgG2a (Pharmingen, Hamburg, Germany) were added to determine IgG subclasses. Plates were incubated for an additional 1 h at 37° C. After four washes, 100 µl of peroxidase-conjugated streptavidin (Pharmingen) was added to cells and plates incubated at 37° C. for 30 min. After four washes, reactions were developed with ABTS in 0.1 M citrate-phosphate buffer (pH 4.35) containing 0.01% $H_2O_2$. To determine the concentration of IgG subclasses in serum, standard curves were obtained by coating the wells with an isotype-specific goat anti-mouse IgG, and then by incubating with purified mouse IgG1 or IgG2 antibodies (Dianova, Hamburg, Germany).

Figure 12:
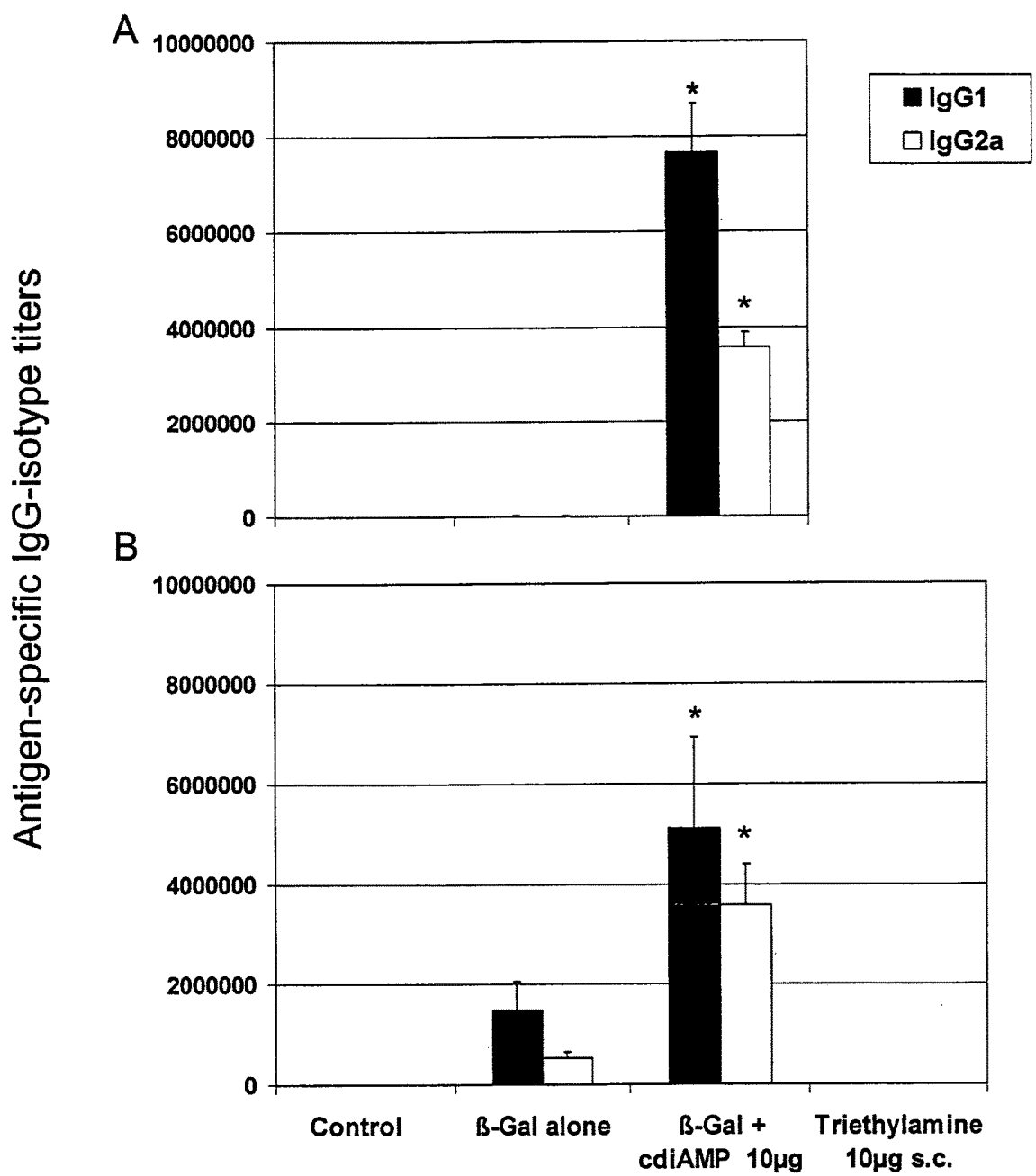
FIG. 12.

The pattern of the different subclasses of the β-gal antigen-specific IgG isotypes present in the sera of vaccinated mice is shown in FIG. 12. FIG. 12A shows the results for intranasal administration of β-Gal alone, β-Gal and c-diAMP. The protocol for vaccination was identical to the protocol described in Example 3. As can be ascertained from FIG. 12A, the amount of antigen specific antibodies of the IgG1 subtype and the IgG2a isotype were strongly increased after intranasal administration of the antigen using c-diAMP as mucosal adjuvant. Further, also in case of systemic administration, here subcutaneous administration, the expression of the IgG1 isotype as well as of th IgG2a isotype are strongly increased, see FIG. 12B. The data represents the average titer of a group of 5 animals.

Thus, the use of c-diAMP allows eliciting a strong antigen-specific antibody response. The triggering can be seen not only after intranasal administration but also after parenteral administration.

Experimental protocol: Spleens from mucosal (i.n.) or parenteral (s.c.) vaccinated mice were removed and pooled for analysis of cellular immune responses. The protocol for vaccination was identical to the protocol described in Example 2. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble β-gal.

To characterize the type of Th response stimulated following immunization, the content of IFNγ, IL-6, IL-10, IL-12 (for c-diAMP only), MCP-1, and TNFα was measured in supernatants from in vitro re-stimulated spleen cells (FIG. 7 and 8 for c-diGMP and FIG. 9 for c-diAMP) by the Cytometric Bead Array. Culture supernatants from proliferating cells were collected on days 2 and 4, and stored at −70° C. Determination of IFNγ, TNFα, IL-6, IL-10, IL-12, and MCP-1 was performed by cytometric bead array (CBA) analysis using the commercial kit from BectonDickinson, according to the manufacturer's instructions or with commercially available ELISA systems. For CBA analysis, a standard curve was generated for each cytokine by using the corresponding recombinant murine cytokines (Pharmingen). Probes were incubated at room temperature for additional 2h. The probes were analyzed subsequently by flow cytometry as described in the protocol of BD.

Figure 7:
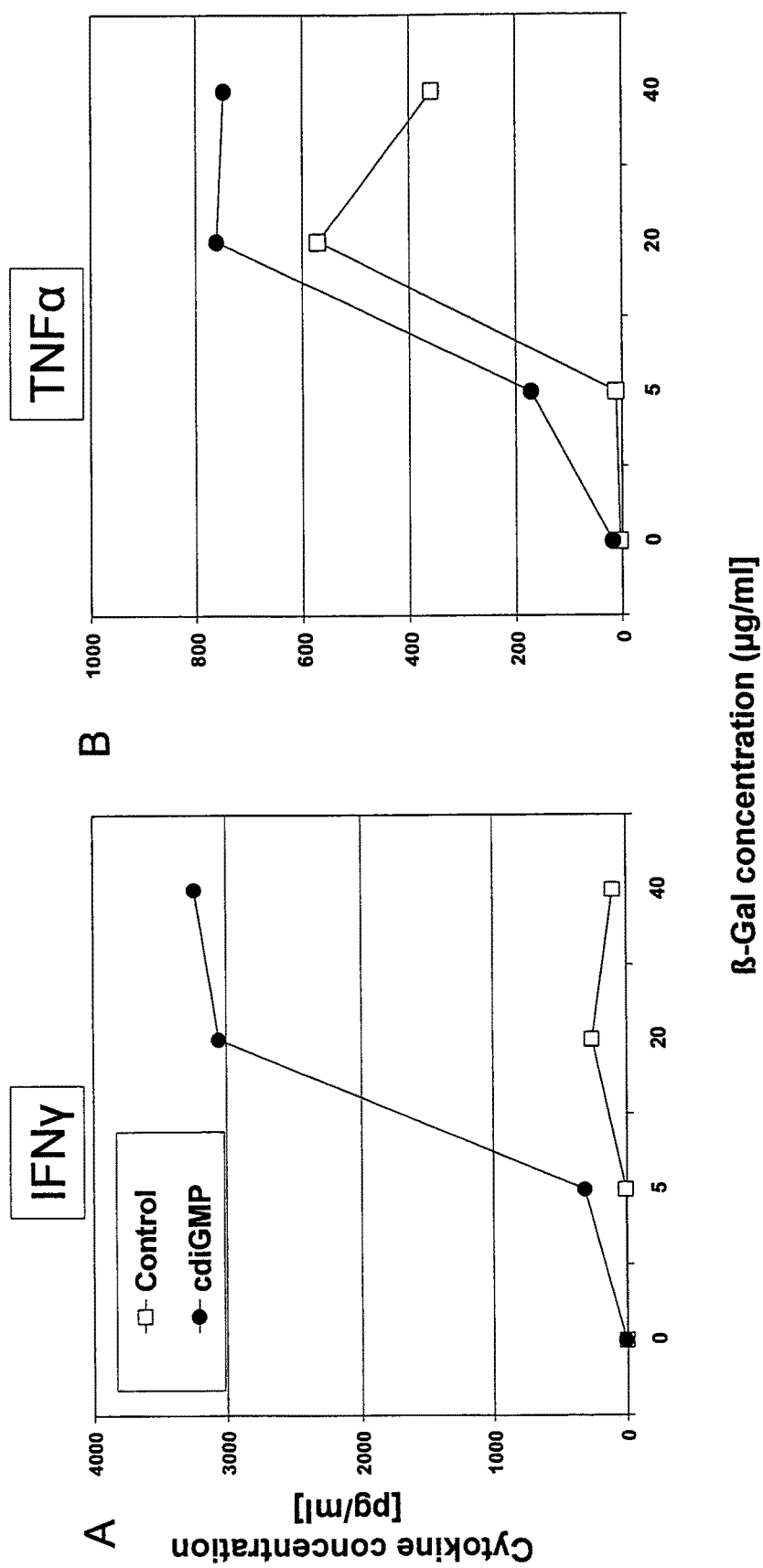
FIG. 7.
Figure 8:
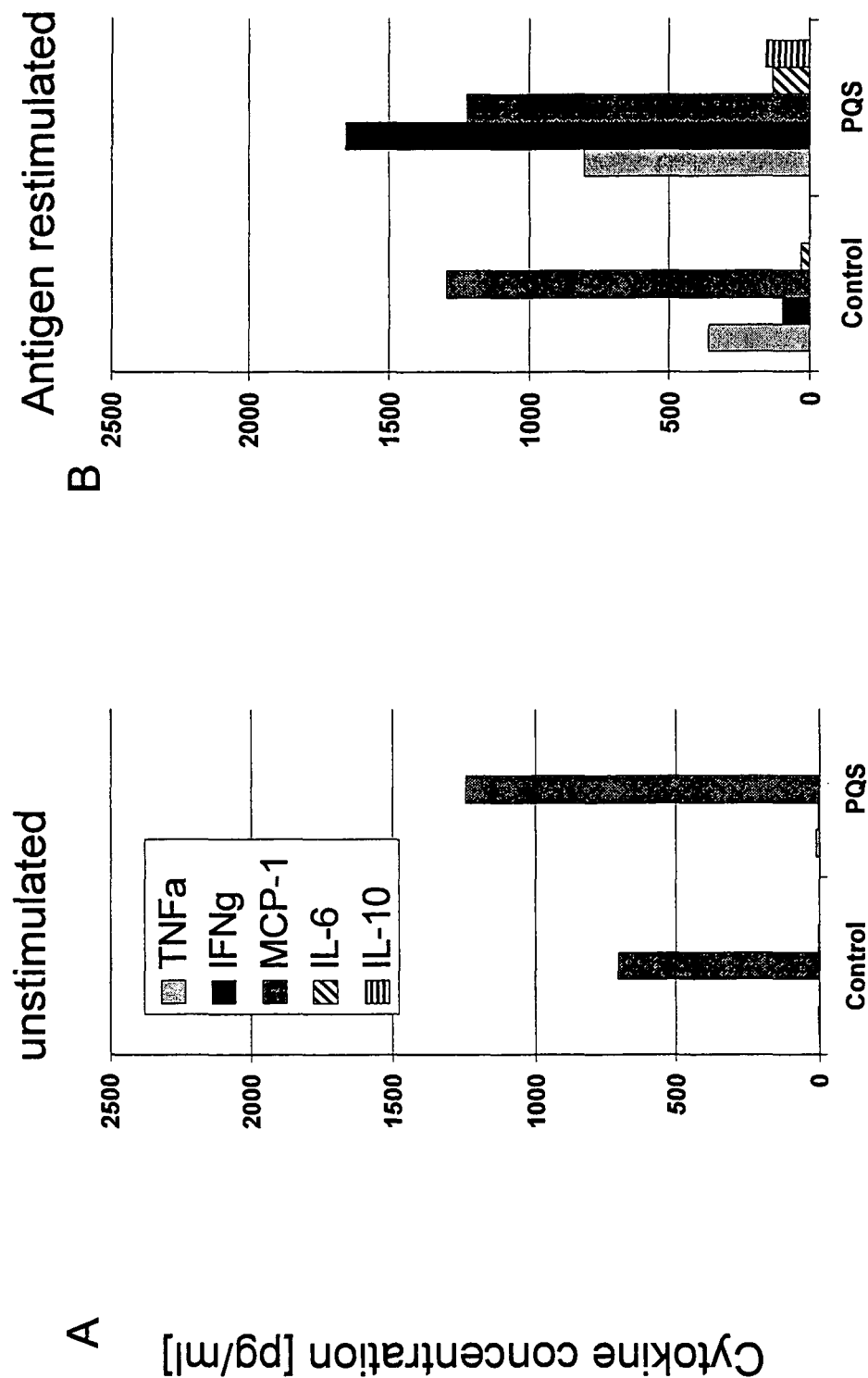
FIG. 8.
Figure 9:
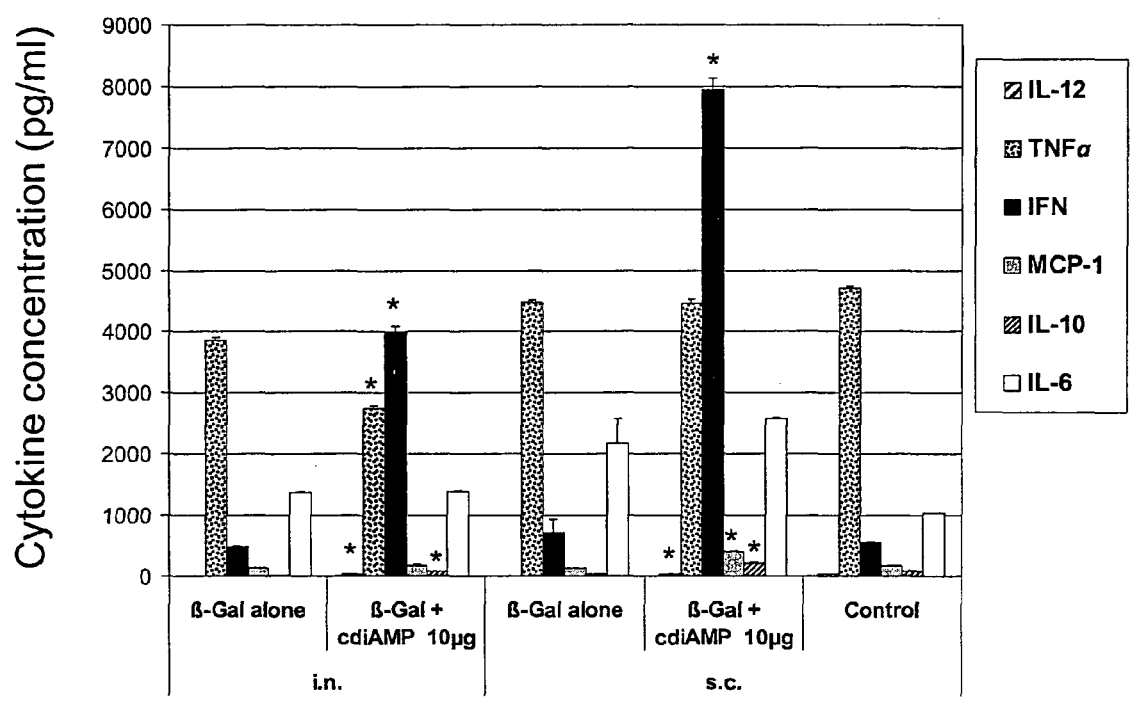
FIG. 9.

The levels of Th1 specific cytokines, such as IFNγ or TNFα, showed enhanced secretion in comparison to the control (β-Gal without additional adjuvant) as shown in FIG. 7 for c-diGMP and IFNy and FIG. 9 for c-diAMP. The same results can be observed for the inflammatory cytokines IL-10 and IL-6, see FIGS. 8 and 9. The data shown for c-diGMP are obtained from spleen cells from intranasal immunized mice.

For c-diAMP the results confirm that a balanced Th1/Th2 response was induced in mice. The results show that not only antigen-specific IFNγ and IL-2 secreting cells, but also IL-4 secreting cells were increased in number in mice receiving c-diGMP and c-diAMP as adjuvant.

6. Analysis of the T Helper Patterns Stimulated by Using c-diGMP and c-diAMP-PEG as Adjuvant by Elispot Experimental protocol: Spleens from vaccinated mice were removed and pooled for analysis of cellular immune responses. The protocol for vaccination was identical to the protocol described in Example 2. Cells were grown in RPMI 1640 supplemented with 10% fetal calf serum, 100 U/ml of penicillin, 50 µg/ml of streptomycin, $5 \times 10^{-5}$ M 2-mercaptoethanol and 1 mM L-glutamine (GIBCO BRL, Karlsruhe, Germany) and maintained at 37° C. in a humidified 5% $CO_2$ atmosphere. Spleen cell suspensions were adjusted to $5 \times 10^6$ cells/ml in complete medium, cells were seeded with 100 µl per well in a flat-bottomed 96-well microtiter plate (Nunc) and plates were incubated for 4 days in the presence of different concentrations of soluble β-Gal.

For coating ELISPOT plates, said plates were incubated with 100 µl/well of purified capture antibody (10 µg/ml in coating buffer) at 4° C. overnight. After 6× washing steps, the plates were blocked with 200 µl/well of complete RPMI-1640 at room temperature for 1 hour. The activated cells were seeded at 100 µl per well and incubate at 37° C., in a 5% $CO_2$ humidified incubator for 24 hours or 48h hours. After 5× washing steps with washing buffer and 1× step with distilled water, 100 µl/well of the biotinylated detection antibody with a concentration of 1 µg/ml in Assay Diluent was added and incubated at room temperature for 2 hrs. After further washing steps 100 µl/well of the AV-HRP at 1/1000 dilution in Assay Diluent was added and incubated at room temperature for 30 minutes. After further washing steps 100 µl/well of AEC Substrate Solution was added and developed at room temperature for 10-60 minutes until visible spots appeared. After washing steps with (3×) with 200 µl/well distilled water, the plates were air-dried and analyzed by counting the spots by an ELISPOT reader. Each concentration was tested in triplicates.

Figure 10:
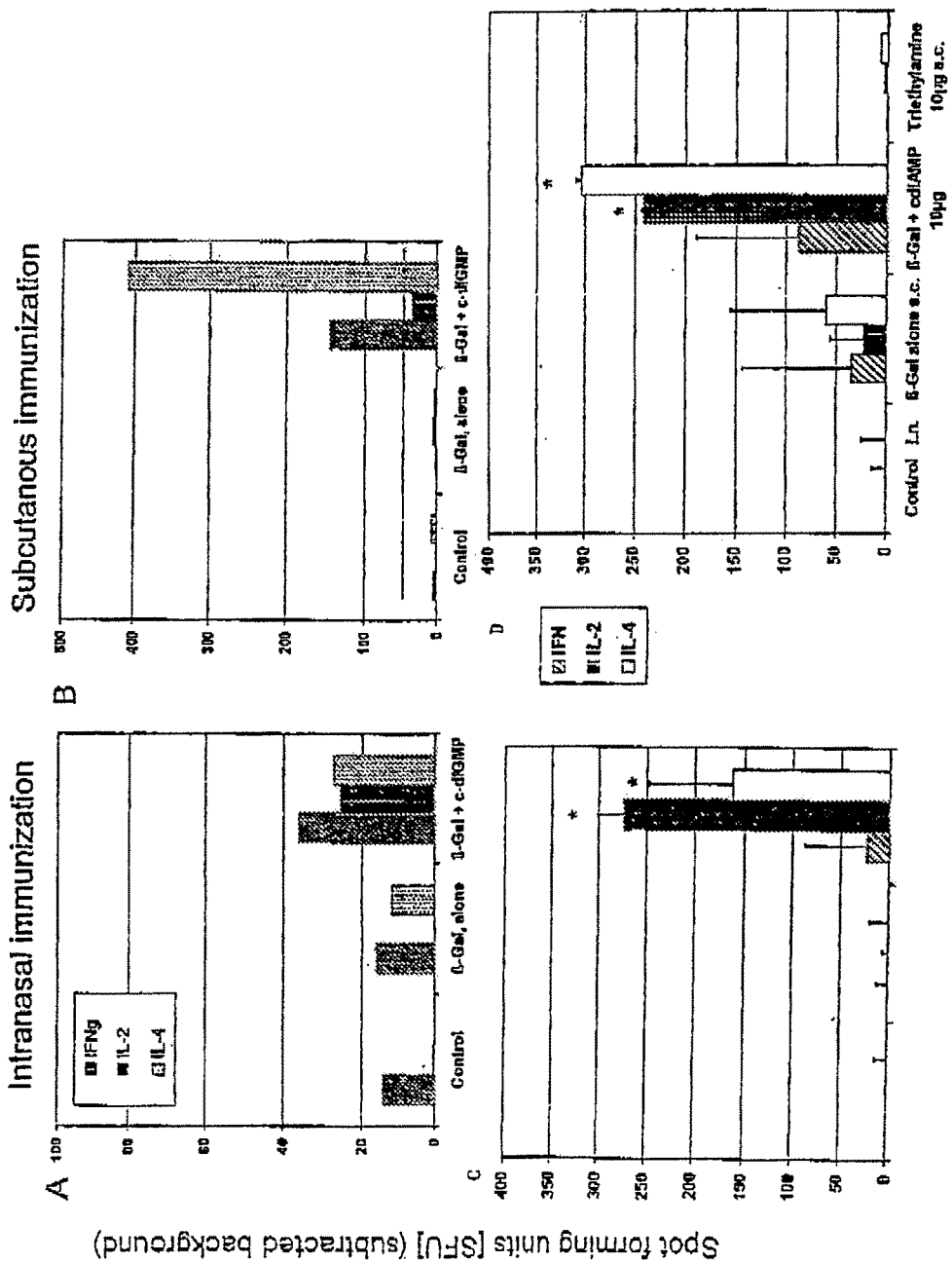
FIG. 10.

An increment in the number of splenic IFNγ producing cells was observed in animals immunized with β-Gal co-administered with c-diGMP or c-diAMP, in response to restimulation with a peptide encompassing the MHC class I-restricted immunodominant epitope from β-Galactosidase (CD8 epitope) after parenteral vaccination (FIG. 10). In contrast, INFγ producing cells were scarcely detectable after i.n. administration of β-Gal. However, i.n. vaccination of β-gal with additional adjuvant c-diGMP, or c-diAMP resulted in amounts of IFNγ expressing cells similar to the level determined after s.c. vaccination, see results for c-diGMP. Furthermore, a strong expression of splenic IL-2 and IL-4 producing cells after restimulation with the β-Gal protein was shown in mice immunized with β-Gal co-administered with the respective adjuvant by the i.n. and by the s.c. route.

The invention claimed is:

1. A method of enhancing an immune response in a subject in need thereof for eliciting a balanced Th1/Th2 response, comprising the step of administering, as an adjuvant with one or more different antigens, to the subject at least one compound according to formula (I)

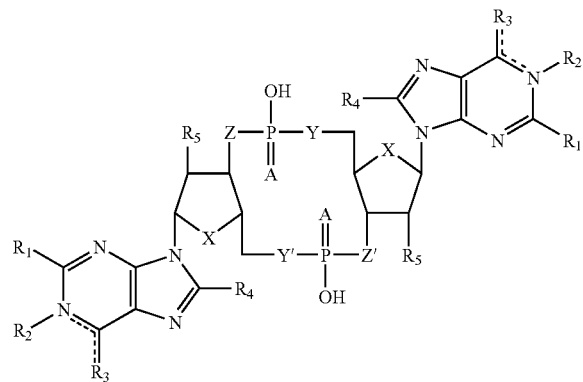

wherein
A is independently S or O;
X is independently S, N, O, CH2;
Y, Y' is independently NH, CH2, O;
Z, Z' is independently NH, CH2, O;
R1 is H;
R2 is H or absent;
R3 is independently NH2, O, OH, H, or a halogen;
R4 is independently H, halogen, or straight or branched C1-C6 alkyl group which may optionally be substituted;
R5 is independently H, OH or a straight or branched C1-C6 alkyl group or a straight or branched C1-C6 alkoxy group which may optionally be substituted;
----- is a single or double bond;
and salts or solvates thereof, wherein said enhanced immune response is to said one or more different antigens.

2. The method according to claim 1 wherein in the compound according to formula (I) the purine residue is selected from the group consisting of an adenine, an inosine, a xanthine, and a hypoxanthine residue.

3. The method according to claim 1 wherein in the compound according to formula (I) R5 is OH, X is O, and Y,Y', Z, and Z' are O.

4. The method according to claim 1 wherein the compound according to formula (I) is a cyclic bis(3'-5')diadenylic acid or a salt or a solvate thereof.

5. The method according to claim 1 wherein the compound of formula (I) is administered in combination with at least one of a pharmaceutically active ingredient, a pharmaceutically acceptable carrier, diluent, preservative, adjuvants other than the compound of formula (I), immunomodulators, or excipient.

6. The method according to claim 1 wherein the adjuvant is provided in a form admixed or co-formulated with an antigen.

7. The method according to claim 1 wherein said adjuvant is in a form suitable for mucosal administration.

8. The method according to claim 7 wherein said adjuvant is administered by a route selected from intranasal, intranasal-associated lymphoid tissue (intra NALT), oral, intra-rectal, intrapulmonary, intrabronchial, intrathecal, conjunctival, intra-vaginal, intra-urethral, administration into the milk ducts of the breast, and inhalation.

9. The method according to claim 1 wherein said adjuvant is in a form suitable for parenteral administration.

10. The method according to claim 9 wherein said adjuvant is administered by a route selected from subcutaneous, intravenous, intradermal, and intra muscular administration.

11. The method according to claim 2 wherein in the compound according to formula (I) the purine residue is selected from the group consisting of an adenine and an inosine.

12. A method of activating the antigen presenting function of antigen presenting cells and eliciting a balanced Th1/Th2 response, comprising the step of administering, as an adjuvant with one or more different antigens, to the subject at least one compound according to formula (I)

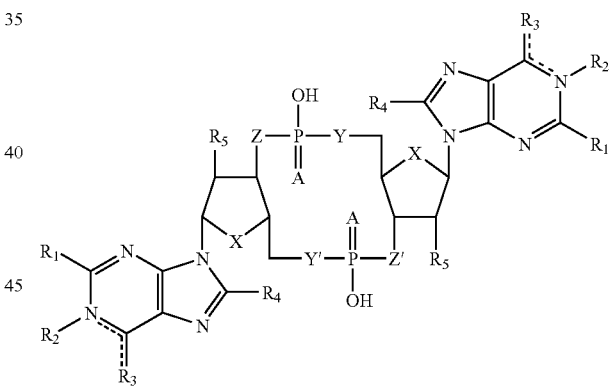

wherein
A is independently S or O;
X is independently S, N, O, CH2;
Y, Y' is independently NH, CH2, O;
Z, Z' is independently NH, CH2, O;
R1 is H;
R2 is H or absent;
R3 is independently NH2, O, OH, H, or a halogen;
R4 is independently H, halogen, or straight or branched C1-C6 alkyl group which may optionally be substituted;
R5 is independently H, OH or a straight or branched C1-C6 alkyl group or a straight or branched C1-C6 alkoxy group which may optionally be substituted;
----- is a single or double bond;
and salts or solvates thereof, wherein said at least one compound according to formula (I) activates the antigen presenting function of antigen presenting cells and said one or more different antigens elicits a balanced Th1/Th2 response.

\* \* \* \* \*